(12) United States Patent
Popp

(10) Patent No.: US 8,591,811 B2
(45) Date of Patent: Nov. 26, 2013

(54) MONITORING ACCEPTANCE CRITERIA OF PHARMACEUTICAL MANUFACTURING PROCESSES

(71) Applicant: Shane M. Popp, Los Angeles, CA (US)

(72) Inventor: Shane M. Popp, Los Angeles, CA (US)

(73) Assignee: SMP Logic Systems LLC, Los Angeles, CA (US)

( * ) Notice: Subject to any disclaimer, the term of this patent is extended or adjusted under 35 U.S.C. 154(b) by 0 days.

(21) Appl. No.: 13/815,713

(22) Filed: Mar. 18, 2013

(65) Prior Publication Data

US 2013/0218317 A1    Aug. 22, 2013

Related U.S. Application Data

(63) Continuation of application No. 12/799,097, filed on Apr. 15, 2010, now Pat. No. 8,491,839, which is a continuation-in-part of application No. 11/503,767, filed on Aug. 14, 2006, now Pat. No. 7,799,273, which is a continuation of application No. 11/500,642, filed on Aug. 8, 2006, now Pat. No. 7,471,991, which is a continuation of application No. 10/840,732, filed on May 6, 2004, now Pat. No. 7,444,197.

(51) Int. Cl.
*G01N 21/00* (2006.01)

(52) U.S. Cl.
USPC .................. 422/67; 422/64; 422/65; 422/66; 436/180; 700/26; 700/109; 700/110

(58) Field of Classification Search
USPC .......... 422/64–67; 436/180; 700/26, 109–110
See application file for complete search history.

(56) References Cited

U.S. PATENT DOCUMENTS

| | | |
|---|---|---|
| 4,443,861 A | 4/1984 | Slater |
| 4,558,413 A | 12/1985 | Schmidt et al. |
| 4,646,229 A | 2/1987 | Boyle |
| 4,687,662 A | 8/1987 | Schobel |
| 4,813,013 A | 3/1989 | Dunn |
| 4,843,575 A | 6/1989 | Crane |
| 4,852,047 A | 7/1989 | Lavallee et al. |
| 4,860,204 A | 8/1989 | Gendron et al. |
| 4,894,511 A | 1/1990 | Caledonia et al. |
| 5,006,992 A | 4/1991 | Skeirik |
| 5,029,179 A | 7/1991 | Harrison |
| 5,038,138 A | 8/1991 | Akiyama et al. |
| 5,041,195 A | 8/1991 | Taylor et al. |
| 5,041,197 A | 8/1991 | Gelb |
| 5,053,608 A | 10/1991 | Senanayake |

(Continued)

FOREIGN PATENT DOCUMENTS

| | | |
|---|---|---|
| EP | 0696001 B1 | 2/1996 |
| EP | 0700680 B1 | 11/1999 |

(Continued)

OTHER PUBLICATIONS

Guidance for Industry 21 CFR Part 11 Electronic Records, Electronic Signatures Validation Draft Guidance, US Department of Health and Human Services, Aug. 2001, pp. 1-24.

(Continued)

*Primary Examiner* — Jyoti Nagpaul

(57) ABSTRACT

Methods of monitoring acceptance criteria of pharmaceutical manufacturing processes are disclosed herein. The methods described herein provide an ability to control and monitor pharmaceutical manufacturing processes (for example, finishing and packaging of pharmaceuticals) and can ensure data and product integrity and ultimately minimize overall manufacturing cost.

14 Claims, 5 Drawing Sheets

(56) References Cited

U.S. PATENT DOCUMENTS

| | | |
|---|---|---|
| 5,084,144 A | 1/1992 | Reddy et al. |
| 5,122,717 A | 6/1992 | Hayashi |
| 5,132,193 A | 7/1992 | Reddy et al. |
| 5,133,842 A | 7/1992 | Taylor et al. |
| 5,134,560 A | 7/1992 | Ferriter et al. |
| 5,191,534 A | 3/1993 | Orr et al. |
| 5,235,605 A | 8/1993 | Rines et al. |
| 5,235,610 A | 8/1993 | Finch et al. |
| 5,247,693 A | 9/1993 | Bristol |
| 5,278,979 A | 1/1994 | Foster et al. |
| 5,301,336 A | 4/1994 | Kodosky et al. |
| 5,315,530 A | 5/1994 | Gerhardt et al. |
| 5,325,481 A | 6/1994 | Hunt |
| 5,345,457 A | 9/1994 | Zenzie et al. |
| 5,358,695 A | 10/1994 | Helble et al. |
| 5,367,624 A | 11/1994 | Cooper |
| 5,377,003 A | 12/1994 | Lewis et al. |
| 5,392,207 A | 2/1995 | Wilson et al. |
| 5,447,708 A | 9/1995 | Helble et al. |
| 5,461,477 A | 10/1995 | Marinelli et al. |
| 5,481,712 A | 1/1996 | Silver et al. |
| 5,528,368 A | 6/1996 | Lewis et al. |
| 5,548,535 A | 8/1996 | Zvonar |
| 5,552,412 A | 9/1996 | Cameron et al. |
| 5,554,822 A | 9/1996 | Gilpin et al. |
| 5,556,447 A | 9/1996 | Srinivasachar et al. |
| 5,565,073 A | 10/1996 | Fraser et al. |
| 5,576,946 A | 11/1996 | Bender et al. |
| 5,586,313 A | 12/1996 | Schnittker et al. |
| 5,603,894 A | 2/1997 | Aikus et al. |
| 5,647,968 A | 7/1997 | Fraser et al. |
| 5,664,112 A | 9/1997 | Sturgeon et al. |
| 5,712,990 A | 1/1998 | Henderson |
| 5,732,397 A | 3/1998 | DeTore et al. |
| 5,734,026 A | 3/1998 | Florin-Robertsson et al. |
| 5,740,190 A | 4/1998 | Moulton |
| 5,767,941 A | 6/1998 | Ferguson |
| 5,774,489 A | 6/1998 | Moulton et al. |
| 5,774,875 A | 6/1998 | Medeiros et al. |
| 5,787,000 A | 7/1998 | Lilly et al. |
| 5,793,013 A | 8/1998 | Read et al. |
| 5,805,442 A | 9/1998 | Crater et al. |
| 5,831,859 A | 11/1998 | Medeiros et al. |
| 5,832,449 A | 11/1998 | Cunningham |
| 5,835,922 A | 11/1998 | Shima et al. |
| 5,847,957 A | 12/1998 | Cohen et al. |
| 5,864,483 A | 1/1999 | Brichta |
| 5,892,947 A | 4/1999 | DeLong et al. |
| 5,901,879 A | 5/1999 | Duhaime et al. |
| 5,953,688 A | 9/1999 | Su et al. |
| 5,956,938 A | 9/1999 | Brandenburg |
| 5,970,503 A | 10/1999 | Eisenberg |
| 5,997,155 A | 12/1999 | Ducharme et al. |
| 5,997,361 A | 12/1999 | Driscoll et al. |
| 6,025,769 A | 2/2000 | Chu et al. |
| 6,034,768 A | 3/2000 | Fraser et al. |
| 6,049,742 A | 4/2000 | Milne et al. |
| 6,055,507 A | 4/2000 | Cunningham |
| 6,067,549 A | 5/2000 | Smalley et al. |
| 6,083,281 A | 7/2000 | Diec et al. |
| 6,106,274 A | 8/2000 | Ritchie et al. |
| 6,112,130 A | 8/2000 | Fukuda et al. |
| 6,123,964 A | 9/2000 | Asgharnejad et al. |
| 6,141,647 A | 10/2000 | Meijer et al. |
| 6,169,928 B1 | 1/2001 | Olson et al. |
| 6,215,898 B1 | 4/2001 | Woodfill et al. |
| 6,223,343 B1 | 4/2001 | Hopwood et al. |
| 6,226,369 B1 | 5/2001 | Lim et al. |
| 6,235,938 B1 | 5/2001 | Hartwig et al. |
| 6,243,615 B1 | 6/2001 | Neway et al. |
| 6,256,640 B1 | 7/2001 | Smalley et al. |
| 6,272,506 B1 | 8/2001 | Bell |
| 6,324,522 B2 | 11/2001 | Peterson et al. |
| 6,347,533 B1 | 2/2002 | Tung |
| 6,370,422 B1 | 4/2002 | Richards-Kortum et al. |
| 6,385,768 B1 | 5/2002 | Ziebell |
| 6,393,458 B1 | 5/2002 | Gigliotti et al. |
| 6,397,115 B1 | 5/2002 | Basden |
| 6,419,953 B1 | 7/2002 | Qiu et al. |
| 6,441,552 B1 | 8/2002 | Brandenburg et al. |
| 6,446,136 B1 | 9/2002 | Pohlmann et al. |
| 6,456,737 B1 | 9/2002 | Woodfill et al. |
| 6,470,227 B1 | 10/2002 | Rangachari et al. |
| 6,483,112 B1 | 11/2002 | Lewis |
| 6,501,869 B1 | 12/2002 | Athale |
| 6,505,085 B1 | 1/2003 | Tuttle et al. |
| 6,509,145 B1 | 1/2003 | Torrianni |
| 6,564,119 B1 | 5/2003 | Vaculik et al. |
| 6,567,788 B1 | 5/2003 | Johnson |
| 6,581,020 B1 | 6/2003 | Buote et al. |
| 6,606,524 B1 | 8/2003 | Byun et al. |
| 6,607,577 B2 | 8/2003 | Vaculik et al. |
| 6,631,630 B1 | 10/2003 | Pourboghrat et al. |
| 6,636,298 B1 | 10/2003 | Bachelder et al. |
| 6,645,529 B2 | 11/2003 | Gergely et al. |
| 6,687,558 B2 | 2/2004 | Tuszynski |
| 6,687,887 B1 | 2/2004 | Teig et al. |
| 6,690,464 B1 | 2/2004 | Lewis et al. |
| 6,690,673 B1 | 2/2004 | Jarvis |
| 6,691,070 B1 | 2/2004 | Williams et al. |
| 6,692,764 B2 | 2/2004 | Katdare et al. |
| 6,697,783 B1 | 2/2004 | Brinkman et al. |
| 6,707,122 B1 | 3/2004 | Hines et al. |
| 6,718,291 B1 | 4/2004 | Shapiro et al. |
| 6,732,019 B2 | 5/2004 | Spool et al. |
| 6,735,748 B1 | 5/2004 | Teig et al. |
| 6,738,450 B1 | 5/2004 | Barford |
| 6,754,543 B1 | 6/2004 | Wold |
| 6,776,486 B2 | 8/2004 | Steele et al. |
| 6,778,882 B2 | 8/2004 | Spool et al. |
| 6,816,793 B2 | 11/2004 | Chow et al. |
| 6,839,604 B2 | 1/2005 | Godfrey et al. |
| 6,850,809 B1 | 2/2005 | Callar et al. |
| 6,852,219 B2 | 2/2005 | Hammond |
| 6,857,112 B1 | 2/2005 | Teig et al. |
| 6,862,488 B2 | 3/2005 | Mansour-Awad |
| 6,865,508 B2 | 3/2005 | Ueki et al. |
| 6,883,148 B1 | 4/2005 | Teig et al. |
| 6,885,907 B1 | 4/2005 | Zhang et al. |
| 6,889,900 B2 | 5/2005 | Davies et al. |
| 6,892,366 B1 | 5/2005 | Teig et al. |
| 6,904,370 B1 | 6/2005 | Levinson et al. |
| 6,905,411 B2 | 6/2005 | Nguyen et al. |
| 6,907,591 B1 | 6/2005 | Teig et al. |
| 6,944,512 B2 | 9/2005 | Breimesser et al. |
| 6,944,662 B2 | 9/2005 | Devine et al. |
| 6,965,895 B2 | 11/2005 | Smith et al. |
| 6,966,235 B1 | 11/2005 | Paton |
| 6,968,292 B2 | 11/2005 | Boyer |
| 6,977,385 B2 | 12/2005 | Struye et al. |
| 6,979,578 B2 | 12/2005 | Venugopal |
| 6,980,852 B2 | 12/2005 | Jersey-Willuhn et al. |
| 7,006,214 B2 | 2/2006 | Rzasa et al. |
| 7,006,882 B2 | 2/2006 | Chang et al. |
| 7,020,876 B1 | 3/2006 | Dietz et al. |
| 7,027,883 B2 | 4/2006 | Shen |
| 7,031,784 B1 | 4/2006 | Lai et al. |
| 7,033,023 B2 | 4/2006 | Steele et al. |
| 7,050,875 B2 | 5/2006 | Cribbs et al. |
| 7,051,293 B1 | 5/2006 | Teig et al. |
| 7,069,101 B1 | 6/2006 | Arackaparambil et al. |
| 7,079,912 B2 | 7/2006 | Stack et al. |
| 7,089,072 B2 | 8/2006 | Chia |
| 7,103,524 B1 | 9/2006 | Teig et al. |
| 7,112,351 B2 | 9/2006 | Affinito |
| 7,113,845 B1 | 9/2006 | Behm et al. |
| 7,123,974 B1 | 10/2006 | Hamilton |
| 7,126,470 B2 | 10/2006 | Clift et al. |
| 7,127,330 B2 | 10/2006 | Spool et al. |
| 7,133,727 B2 | 11/2006 | Van Dyk et al. |
| 7,154,102 B2 | 12/2006 | Poteet et al. |
| 7,162,534 B2 | 1/2007 | Schleiss et al. |
| 7,169,107 B2 | 1/2007 | Jersey-Willuhn et al. |
| 7,172,115 B2 | 2/2007 | Lauden |

(56) References Cited

U.S. PATENT DOCUMENTS

| | | |
|---|---|---|
| 7,174,230 B2 | 2/2007 | Arackaparambil et al. |
| 7,174,353 B2 | 2/2007 | Friske et al. |
| 7,184,820 B2 | 2/2007 | Jersey-Willuhn et al. |
| 7,184,964 B2 | 2/2007 | Wang |
| 7,187,992 B2 | 3/2007 | Tuszynski |
| 7,197,405 B1 | 3/2007 | Pruett et al. |
| 7,207,481 B2 | 4/2007 | Barenburg et al. |
| 7,207,505 B2 | 4/2007 | Bender et al. |
| 7,216,007 B2 | 5/2007 | Johnson |
| 7,216,084 B2 | 5/2007 | Brinkman et al. |
| 7,231,398 B2 | 6/2007 | Schlereth et al. |
| 7,233,830 B1 | 6/2007 | Callaghan et al. |
| 7,240,119 B2 | 7/2007 | Ascoli et al. |
| 7,249,356 B1 | 7/2007 | Wilson et al. |
| 7,252,572 B2 | 8/2007 | Wright et al. |
| 7,257,501 B2 | 8/2007 | Zhan et al. |
| 7,269,640 B2 | 9/2007 | Huntley, Jr. et al. |
| 7,280,893 B2 | 10/2007 | Spool et al. |
| 7,299,102 B2 | 11/2007 | Ouchi |
| 7,302,307 B1 | 11/2007 | Anderson et al. |
| 7,305,278 B2 | 12/2007 | Enright et al. |
| 7,317,959 B2 | 1/2008 | Pfander et al. |
| 7,323,991 B1 | 1/2008 | Eckert et al. |
| 7,343,605 B2 | 3/2008 | Langkafel et al. |
| 7,347,613 B2 | 3/2008 | Ditzig et al. |
| 7,359,760 B2 | 4/2008 | Kishi et al. |
| 7,367,242 B2 | 5/2008 | Xi et al. |
| 7,441,030 B1 | 10/2008 | Smith et al. |
| 7,446,406 B2 | 11/2008 | Mizuno et al. |
| 7,465,417 B2 | 12/2008 | Hutson et al. |
| 7,471,992 B2 | 12/2008 | Schmidt et al. |
| 7,493,310 B2 | 2/2009 | Eryurek et al. |
| 7,533,798 B2 | 5/2009 | Jones et al. |
| 7,606,681 B2 | 10/2009 | Esmaili et al. |
| 7,607,913 B2 | 10/2009 | Wells |
| 7,636,449 B2 | 12/2009 | Mirtich et al. |
| 7,643,892 B2 | 1/2010 | Moor et al. |
| 7,647,126 B2 | 1/2010 | Blevins et al. |
| 7,668,613 B2 | 2/2010 | Baier et al. |
| 7,702,401 B2 | 4/2010 | Eryurek et al. |
| 7,771,988 B2 | 8/2010 | Amano |
| 7,788,047 B2 | 8/2010 | Schick et al. |
| 2001/0042068 A1 | 11/2001 | Yoshida et al. |
| 2001/0054032 A1 | 12/2001 | Goldman et al. |
| 2002/0007422 A1 | 1/2002 | Bennett |
| 2002/0011852 A1 | 1/2002 | Mandelis et al. |
| 2002/0015176 A1 | 2/2002 | Takao et al. |
| 2002/0044128 A1 | 4/2002 | Hayashi et al. |
| 2002/0046290 A1 | 4/2002 | Andersson et al. |
| 2002/0113151 A1 | 8/2002 | Forber Jones et al. |
| 2002/0116083 A1 | 8/2002 | Schulze |
| 2002/0128886 A1 | 9/2002 | Wang |
| 2002/0138510 A1 | 9/2002 | Tan |
| 2002/0147569 A1 | 10/2002 | Lay et al. |
| 2002/0156548 A1 | 10/2002 | Arackaparambil et al. |
| 2002/0165806 A1 | 11/2002 | Kataria et al. |
| 2002/0187137 A1 | 12/2002 | Bates et al. |
| 2002/0198964 A1 | 12/2002 | Fukazawa et al. |
| 2003/0018400 A1 | 1/2003 | Tuttle et al. |
| 2003/0040844 A1 | 2/2003 | Spool et al. |
| 2003/0040845 A1 | 2/2003 | Spool et al. |
| 2003/0041016 A1 | 2/2003 | Spool et al. |
| 2003/0041017 A1 | 2/2003 | Spool et al. |
| 2003/0041037 A1 | 2/2003 | Spool et al. |
| 2003/0041038 A1 | 2/2003 | Spool et al. |
| 2003/0041039 A1 | 2/2003 | Spool et al. |
| 2003/0046252 A1 | 3/2003 | Spool et al. |
| 2003/0069795 A1 | 4/2003 | Boyd et al. |
| 2003/0074223 A1 | 4/2003 | Hickle |
| 2003/0125904 A1 | 7/2003 | Ueki et al. |
| 2003/0139939 A1 | 7/2003 | Spool et al. |
| 2003/0149501 A1 | 8/2003 | Tuszynski |
| 2003/0149608 A1 | 8/2003 | Kall et al. |
| 2003/0149717 A1 | 8/2003 | Heinzman |
| 2003/0150909 A1 | 8/2003 | Markham et al. |
| 2003/0154144 A1 | 8/2003 | Pokorny et al. |
| 2003/0172371 A1 | 9/2003 | Offenmuller |
| 2003/0176981 A1 | 9/2003 | Chow et al. |
| 2003/0180957 A1 | 9/2003 | Koopmann et al. |
| 2003/0183777 A1 | 10/2003 | Struye et al. |
| 2003/0200130 A1 | 10/2003 | Kall et al. |
| 2003/0207795 A1 | 11/2003 | Pilon et al. |
| 2003/0216630 A1 | 11/2003 | Jersey-Willuhn et al. |
| 2003/0216662 A1 | 11/2003 | Jersey-Willuhn et al. |
| 2003/0216663 A1 | 11/2003 | Jersey-Willuhn et al. |
| 2003/0223033 A1 | 12/2003 | Steele et al. |
| 2003/0225124 A1 | 12/2003 | Spireas |
| 2004/0006453 A1 | 1/2004 | Gluhovsky et al. |
| 2004/0006486 A1 | 1/2004 | Schmidt et al. |
| 2004/0011288 A1 | 1/2004 | Affinito |
| 2004/0015521 A1 | 1/2004 | Hudicka |
| 2004/0032592 A1 | 2/2004 | Venugopal et al. |
| 2004/0032593 A1 | 2/2004 | Venugopal |
| 2004/0034543 A1 | 2/2004 | Bartsch |
| 2004/0068454 A1 | 4/2004 | Jacobus et al. |
| 2004/0068455 A1 | 4/2004 | Jacobus et al. |
| 2004/0077075 A1 | 4/2004 | Jensen et al. |
| 2004/0078732 A1 | 4/2004 | Meaney |
| 2004/0107415 A1 | 6/2004 | Melamed et al. |
| 2004/0117126 A1 | 6/2004 | Fetterman et al. |
| 2004/0123864 A1 | 7/2004 | Hickey et al. |
| 2004/0133289 A1 | 7/2004 | Larsson et al. |
| 2004/0153171 A1 | 8/2004 | Brandt et al. |
| 2004/0155202 A1 | 8/2004 | Poteet et al. |
| 2004/0158475 A1 | 8/2004 | Juzeszyn et al. |
| 2004/0167648 A1 | 8/2004 | Tuszynski |
| 2004/0176877 A1 | 9/2004 | Hesse et al. |
| 2004/0177055 A1 | 9/2004 | Heidemann et al. |
| 2004/0186648 A1 | 9/2004 | Zheng et al. |
| 2004/0204972 A1 | 10/2004 | Anant et al. |
| 2004/0205406 A1 | 10/2004 | Kaliappan et al. |
| 2004/0243260 A1 | 12/2004 | Law et al. |
| 2005/0012895 A1 | 1/2005 | Steele et al. |
| 2005/0015166 A1 | 1/2005 | Kataria et al. |
| 2005/0015741 A1 | 1/2005 | Langkafel et al. |
| 2005/0033468 A1 | 2/2005 | Pate et al. |
| 2005/0033977 A1 | 2/2005 | Zurita et al. |
| 2005/0038565 A1 | 2/2005 | Power et al. |
| 2005/0055110 A1 | 3/2005 | Tuszynski |
| 2005/0065818 A1 | 3/2005 | Brinkman et al. |
| 2005/0106355 A1 | 5/2005 | Kohlman et al. |
| 2005/0107895 A1 | 5/2005 | Pistikopoulos et al. |
| 2005/0137735 A1 | 6/2005 | Loy et al. |
| 2005/0143851 A1 | 6/2005 | Scalfani et al. |
| 2005/0197786 A1 | 9/2005 | Kataria et al. |
| 2005/0251276 A1 | 11/2005 | Shen |
| 2005/0267611 A1 | 12/2005 | Ishigaki |
| 2005/0278052 A1 | 12/2005 | Bett et al. |
| 2005/0288979 A1 | 12/2005 | Guest |
| 2006/0000470 A1 | 1/2006 | Clarke et al. |
| 2006/0002986 A1 | 1/2006 | Clarke et al. |
| 2006/0010426 A1 | 1/2006 | Lewis et al. |
| 2006/0013473 A1 | 1/2006 | Woodfill et al. |
| 2006/0015536 A1 | 1/2006 | Buchanan et al. |
| 2006/0016830 A1 | 1/2006 | Clarke et al. |
| 2006/0017916 A1 | 1/2006 | Clarke et al. |
| 2006/0020578 A1 | 1/2006 | Hood |
| 2006/0026193 A1 | 2/2006 | Hood |
| 2006/0035395 A1 | 2/2006 | Venugopal |
| 2006/0047453 A1 | 3/2006 | Reeve et al. |
| 2006/0047705 A1 | 3/2006 | Reade et al. |
| 2006/0056732 A1 | 3/2006 | Holmes |
| 2006/0064182 A1 | 3/2006 | Ford, Jr. et al. |
| 2006/0070014 A1 | 3/2006 | Liu et al. |
| 2006/0074522 A1 | 4/2006 | Liang et al. |
| 2006/0074599 A1 | 4/2006 | Emigholz et al. |
| 2006/0074917 A1 | 4/2006 | Chand et al. |
| 2006/0089739 A1 | 4/2006 | Sherriff et al. |
| 2006/0095545 A1 | 5/2006 | Dreyer et al. |
| 2006/0100786 A1 | 5/2006 | Choi |
| 2006/0124443 A1 | 6/2006 | Tuschel et al. |
| 2006/0129259 A1 | 6/2006 | Tornquist et al. |
| 2006/0129265 A1 | 6/2006 | Ouchi |
| 2006/0149407 A1 | 7/2006 | Markham et al. |

(56) References Cited

U.S. PATENT DOCUMENTS

| | | |
|---|---|---|
| 2006/0155410 A1 | 7/2006 | Yamartino |
| 2006/0167579 A1 | 7/2006 | Fujii et al. |
| 2006/0184264 A1 | 8/2006 | Willis et al. |
| 2006/0199260 A1 | 9/2006 | Zhang et al. |
| 2006/0206368 A1 | 9/2006 | Bamberger et al. |
| 2006/0208191 A1 | 9/2006 | Kessler et al. |
| 2006/0214948 A1 | 9/2006 | Murthy |
| 2006/0239116 A1 | 10/2006 | Ditzig et al. |
| 2006/0259163 A1 | 11/2006 | Hsiung et al. |
| 2006/0259500 A1 | 11/2006 | Hood et al. |
| 2006/0267852 A1 | 11/2006 | Ahn et al. |
| 2006/0282223 A1 | 12/2006 | Lewis et al. |
| 2007/0005307 A1 | 1/2007 | Sato |
| 2007/0016542 A1 | 1/2007 | Rosauer et al. |
| 2007/0023513 A1 | 2/2007 | Andreasson et al. |
| 2007/0050070 A1 | 3/2007 | Strain et al. |
| 2007/0061166 A1 | 3/2007 | Ramasubramanian et al. |
| 2007/0067458 A1 | 3/2007 | Chand |
| 2007/0104949 A1 | 5/2007 | Bunge |
| 2007/0122911 A1 | 5/2007 | Browning et al. |
| 2007/0142941 A1 | 6/2007 | McGreevy et al. |
| 2007/0144240 A1 | 6/2007 | Andle |
| 2007/0149586 A1 | 6/2007 | Giordani et al. |
| 2007/0200781 A1 | 8/2007 | Ahn et al. |
| 2007/0214520 A1 | 9/2007 | Scheibel et al. |
| 2007/0239367 A1 | 10/2007 | Odegard et al. |
| 2008/0009959 A1 | 1/2008 | Enright et al. |
| 2008/0015714 A1 | 1/2008 | Rudnick et al. |
| 2008/0066019 A1 | 3/2008 | Worek et al. |
| 2008/0077617 A1 | 3/2008 | Schulz et al. |
| 2008/0082186 A1 | 4/2008 | Hood et al. |
| 2008/0109090 A1 | 5/2008 | Esmaili et al. |
| 2008/0127186 A1 | 5/2008 | Kanodia et al. |
| 2008/0133030 A1 | 6/2008 | Torigoe |
| 2008/0161958 A1 | 7/2008 | Davidson et al. |
| 2009/0043407 A1 | 2/2009 | Mathiesen et al. |
| 2009/0048816 A1 | 2/2009 | Srinivasa et al. |
| 2009/0081723 A1 | 3/2009 | Amano et al. |
| 2009/0117647 A1 | 5/2009 | Buddhi Srinivasa et al. |
| 2009/0149981 A1 | 6/2009 | Evans et al. |
| 2009/0170544 A1 | 7/2009 | Nakagawa |
| 2009/0303490 A1 | 12/2009 | Asano et al. |
| 2009/0312851 A1 | 12/2009 | Mishra |
| 2010/0004771 A1 | 1/2010 | Fahl et al. |
| 2010/0019898 A1 | 1/2010 | Porrazza |
| 2010/0042376 A1 | 2/2010 | Weatherhead |
| 2010/0078841 A1 | 4/2010 | Herrmann et al. |
| 2010/0094449 A1 | 4/2010 | Boeckx et al. |
| 2010/0169639 A1 | 7/2010 | Jeffries et al. |
| 2010/0200660 A1 | 8/2010 | Moed et al. |

FOREIGN PATENT DOCUMENTS

| | | |
|---|---|---|
| EP | 0999506 A1 | 10/2000 |
| EP | 1117007 A2 | 7/2001 |
| EP | 1136951 A2 | 9/2001 |
| EP | 0593114 B1 | 2/2002 |
| EP | 1349177 A2 | 10/2003 |
| EP | 0503521 B2 | 11/2005 |
| EP | 1481294 B1 | 10/2006 |
| EP | 1714695 A1 | 10/2006 |
| EP | 1830386 A2 | 5/2007 |
| EP | 1798814 A2 | 6/2007 |
| WO | WO 97/16434 A1 | 5/1997 |
| WO | WO 01/15705 A1 | 3/2001 |
| WO | WO 02/16924 A1 | 2/2002 |
| WO | WO 02/087546 A2 | 11/2002 |
| WO | WO 03/058533 A1 | 7/2003 |
| WO | WO2004/059531 A1 | 7/2004 |
| WO | WO2004/072868 A1 | 8/2004 |
| WO | WO2004/107087 A2 | 12/2004 |
| WO | WO 2005/038821 A2 | 4/2005 |
| WO | WO2006/017808 A2 | 7/2006 |
| WO | WO2006/069797 A1 | 7/2006 |
| WO | WO 2007/017552 A1 | 2/2007 |
| WO | WO2007/017738 A2 | 2/2007 |
| WO | WO 2007/050013 A1 | 5/2007 |

OTHER PUBLICATIONS

General Principles of Software Validation; Final Guidance for Industry and FDA Staff, pp. i-iv, pp. 1-47, Jan. 11, 2002.

Guide to Inspection of Computerized Systems in Drug Processing, National Center for Drugs and Biologics, et. al. pp. 1-27, Feb. 1983.

The Interoduction of Process Analytical Technology, Using Near Infrared Analysis, to a Pharmaceutical Blending Process, Naicker, et. al., Mar. 6, 2007.

Quality Management System (QMS) for Active Pharmaceutical Ingredient (API) Manufacturers, Inegrating GMP (ICH Q7a) into ISO (9001:2000), pp. 1-73, Sep. 2005.

There is no Execution without Integration, MES Adoption drives performance, pp. 1-21, The Aberdeen Group, Mar. 2007.

The Effect of Shear Mixing on the Blending of Cohesive Lubricants and Drugs, Llusa, et. al., Pharma. Tech., pp. 1-7, Dec. 1, 2005.

Guidance for Management of Computers and Software in Laboratories with Reference to ISO/IEC 17025/2005, EuroLab Technical Report, pp. 1-31, Oct. 2006.

Nondestructive and On-Line Monitoring of Tablets Using Light-Induced Flourescence Technology, Lai, et. al., AAPS PharmaSciTech 2004; 5(1) Article 3.

SAX: Solution Atomization and SonoXrystallization; Technology for Manufacture of Micro and Nanocrystalline Drug Particles, Ruecroft, et. al., pp. 1-27 (2006).

Effects of Average Signed Area Between Two Item Characteristic Curves and Test Purification Procedures on the DIF Detection via the Mantel-Haenszel Method, Wang, et. al., 2004.

Efficiency of the Mantel . . . and Logistic Discriminant Function Analysis Methods in Detecting Differential Item Functioning for Polytomous Items, Su, et. al., 18(4) 313-350 2005.

A Model for Integrating Material Management in a Production Environment, Ham, et. al., Paper No. AUTOW-P109, pp. 1-9, May 3, 2004.

Near-Infrared Spectroscopy and Imaging: Basic Principles and Pharmaceutical Applications, Reich, Adv. Drug Delivery Rev. 57 (2005) pp. 1109-1143.

Small Changes, Big Effects in Biological Manufacturing, Bush, Pharma. Sci. & Tech. News, Nov. 2004, pp. 16-18.

The Role of PAT in Developing New Products, Kraunsoe, APACT Presentation, Apr. 20, 2005, pp. 1-28.

Fit Indices Versus Test Statistics, Yuan, Multivariate Behavioral Research, 40(1), 115-148 (2005).

Using Cycle Time Analysis to Enhance Operations and Improve Yield, Dream, Pharm. Eng. Sep./Oct. 2006, pp. 1-6.

Standard for Software Component Testing, BCS SIGIST, Draft Apr. 27, 2001, pp. 1-67.

Software Testing: Advanced Level Syllabus, ISTQB, Sep. 2003, pp. 1-42.

Council for Education in Pharmaceutical Medicine, IFAPP Oct. 8, 2003, pp. 1-9.

Terahertz Sources and Detectors and Thier Application to Biological Sensing, Crowe, et. al., Phil. Trans. R. Soc. Lond. A (2004) 362, 365-377 (online Dec. 16, 2003).

Validation and Compliance; Software Systems Prepare Manufacturers for Com(PAT)ibility, Rios, Pharma. Tech., May 2004, pp. 1-8.

Use of Impedance Methods in Pharmaceutical Methods, Moldenhauer, Rapid Micro. Newsletter, Jul./Aug. 2003 vol. 2 Issue 3 pp. 1-6.

Process Analytical Technology; Concepts and Principles, Balboni, Pharma. Tech. Oct. 2003, pp. 1-6.

Optical, Tunable Filter-Based micro-Instrumentation for Indusrial Applications, Kotidis, et. al. Oct. 20, 2003, pp. 1-14.

Opening the PAT Toolbox, Folestad, et. al., Eur. Pharma. Rev. (2003) vol. 8; Part 4, pp. 36-42.

The Effects of Physical Parameters on LIBS Analysis of Intact Tablets, Archambault, et. al., AAPS Pharma. Sci. Tech., pp. 1-39, Apr. 19, 2005.

(56) References Cited

OTHER PUBLICATIONS

Quantitative Analysis of Film Coating in a Pan Coater Based on In-Line Sensor Measurements, Perez-Ramos, et. al.. AAPS Pharma. Sci. Tech. Feb. 2, 2005, pp. 1-40.
Stable Isotopes Provide a New PAT Tool, Jasper, et. al., Pharm. Mfg., 2005, 4(5): 28-33. (May 2005).
Process Analytical Technology Case Study, Part I: Feasibility Studies for Quantitative Nir Method Development, Cogdill, et. al., AAPS Pharm. Sci. Tech. Feb. 2, 2004.
Process Analytical Technology Case Study, Part II: Development and Validation of Quantitative Near Infrared Calibrations . . . Cogdill, et. al., AAPS PharsSciTech. Apr. 19 2005.
Process Analytical Technology (PAT) and Scable Automation for Bioprocess Control and Monitoring—A Case Study, Ganguly, et. al., Pharm. Eng. Jan./Feb. 2006 pp. 1-9.
Process Analytical Technology Outsourcing—Impacts on Manufacturing and Process Knowledge, Radspinner, et. al. GOR vol. 7, No. 4 pp. 55-58 Winter 2005.
Real-Time On-Line Monitoring of Fluid Bed Dryers Using NIR Spectroscopy, Das, et. al. May 16, 2005.
Whitepaper, Emerson Process Management Manufacturing Execution Systems Capabilities, Mar. 2007, pp. 1-27.
System Validation with Experion PKS, Whitepaper Honeywell, Sep. 13, 2002, pp. 1-19.
Trends in Integrated Manufacturing, Supplement of BioProcess Internation, Sep. 2004, pp. 1-39.
Global Manufacturing: MES and Beyond Benckmark Report, Aberdeen Group, pp. 1-27. (May 2006).
Elastic-Plastic Behavior and Limit Load Analysis of Pipe Bends Under Out-Of-Plane Moment Loading and Internal Pressure, Mourad, Univ. of Cairo, Dec. 1999, pp. 1-188.
Fundamental Modeling and Simulation of Pharmaceutical Powder Blending, Ngai, May 27, 2003, pp. 1-21.
Compliant Manufacturing with SAP in the Pharmaceutical Industry, Sabogal, et. al., Pharm. Ind. 66, Nr. 11a 1405-1412 (2004).
Challenges and Issues in Veterinary Pharmacology and Animal Health 2004—Preface, Martinez, et. al. AAPS Journal 2005; 7(2) Art. 26, pp. 266-271.
Acoustic-Resonance Spectrometry as a Process Analytical Technology for Rapid and Accurate Tablet Identification, Medendorp, et. al. AAPS Pharm. Sci. Tech 2006; 7(1) Art 25.
In-Line Process Analysis of Residual Moisture in a Fluid Bed Granulator-Dryer using NIR Spectroscopy, Mattes, et. al. Spectroscopy, Jan. 2005.
Experimental Designs at the Crossroads of Drug Discovery, Olsen, Umea university (2006), pp. 1-80.
In-Situ Studies of Sulfamerazine and Carbamazepine Crystallization, Rivera, Univ. of Puerto Rico Thesis (2005) pp. 1-82.
Guidance for Industry; PAT—A Framework for Innovative Pharmaceutical Development, Manufacturing, and Quality Assurance, Sep. 2004 pp. 1-19.
Guidance for Industry, FDA Reviewers and Compliance Guide on: Off-the-Shelf Software Use in Medical Devices, U.S. DHHS, Sep. 9, 1999, pp. 1-26.
Compliance Information on 21 C.F.R Part 11; Rockwell Automation Whitepaper, Jan. 2001, pp. 1-29.
Streamlined Recipe Rollout: Application Profile, Rockwell Automation, Mar. 2001, pp. 1-4.
NIST—Software Error Analysis; NIST Special Publication 500-209, Peng, et. al., Mar. 1993, pp. 1-103.
Process Control System Just the Right Prescription: Application Profile, Rockwell Automation, Mar. 2001, pp. 1-4.
International Conference on Harmonisation of Technical Requirements for Registration of Pharmaceuticals for Human Use; Q9: Quality Risk Management, Nov. 11, 2003, pp. 1-3.
International Conference on Harmonisation of Technical Requirements for Registration of Pharmaceuticals for Human Use; Q8: Pharmaceutical Development, Oct. 8, 2003, pp. 1-4.
Multivariate Analysis and Optimization of Process Variable Trajectories for Batch Processes, Duchesne, et. al., Chemo. and Intell. Lab. Sys. vol. 51, pp. 125-137 (2000).
Barco Launches PlantMaster at K2004, Dusseldorf, Press Release dated Oct. 13, 2004.
Process Control and Instrumentation, GEA Niro A/S, Oct. 1996, pp. 1-4.
Real-time process determination to achieve reproducible coating results, Walter, Aeromatic-Fielder AG, CH-4416 Bubendorf, Apr. 3, 2002, pp. 1-9.
IEEE Standard for Software Safety Plans, Software Eng. Standards Committee, IEEE Standards Board, pp. 1-23, Mar. 17, 1994.
VisioNIR from Uhlmann VisioTec Provides an Existing Solution for FDA's PAT Program, Uhlmann ViseoTec, Unit Dose Alert Jun. 2006, pp. 14-15.
Weigh Dispense Optimization, Rockwell Automation White Paper, pp. 1-13, Mar. 2003.
XFP: A Paperless Manufacturing Solution Dedicated to FDA / GMP Regulated Industries (advertisement), Pharma. Tech. vol. 26, No. 4 pp. 1-4 (Apr. 2002).
Computerized Dispensing System—"CDS", Weigh Ahead Systems Pty. Ltd., Presented at Automation '92, pp. 91-141 (Apr. 29-May 1, 1992).
Chanel, Inc. Computerizes Manufacturing and Data Collection, Manufacturing Case Study, Global Cosmetic Industry Magazine, pp. 50-52 (Jun. 2002).
Validatable Solutions for Pharmaceutical Manufacturing, Square D Groupe Schneider, White Paper, pp. 1-28, May 1995.
Introduction to the PI Management Module XFP Version 4.5, Elan Software Systems, pp. 1-12 (Oct. 18, 2002).

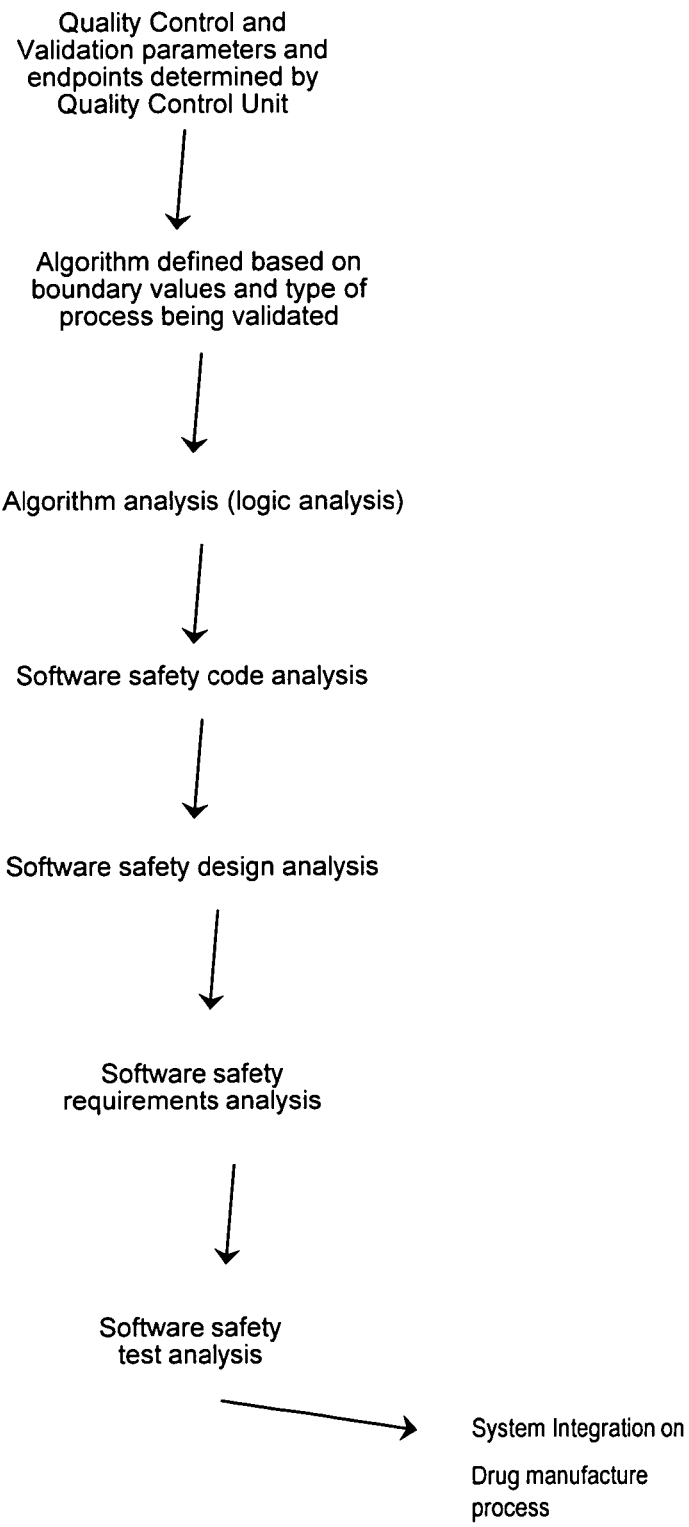
Figure 1: Schematic of Analysis Method

Figure 2. Standard Hazard Analysis and Mitigation Flowchart
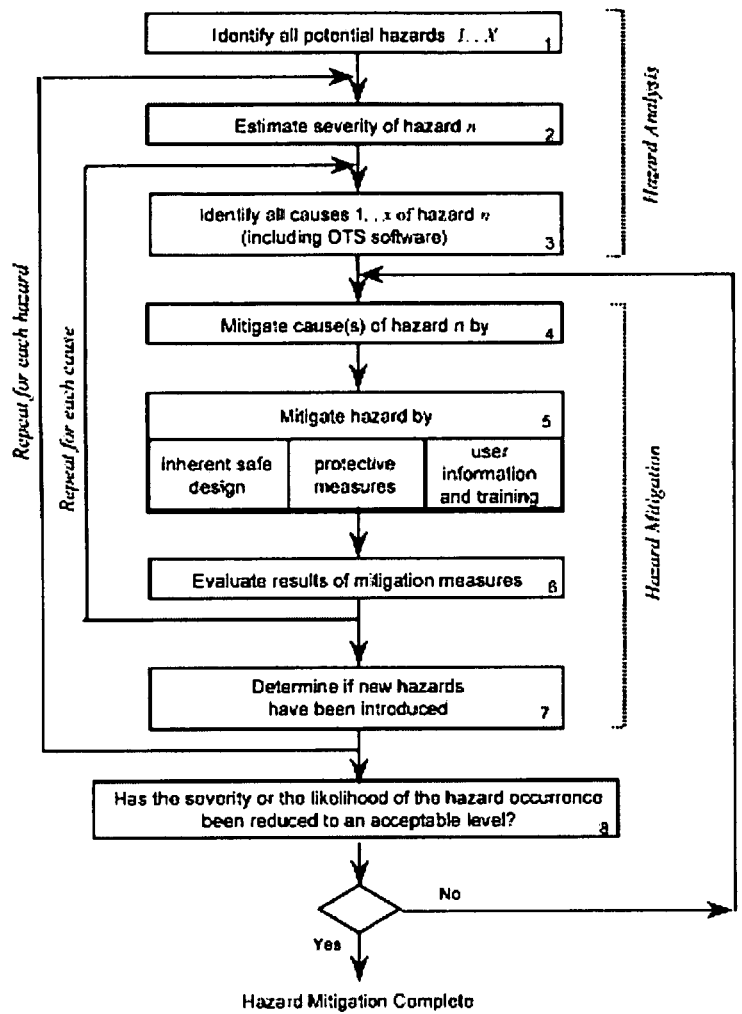

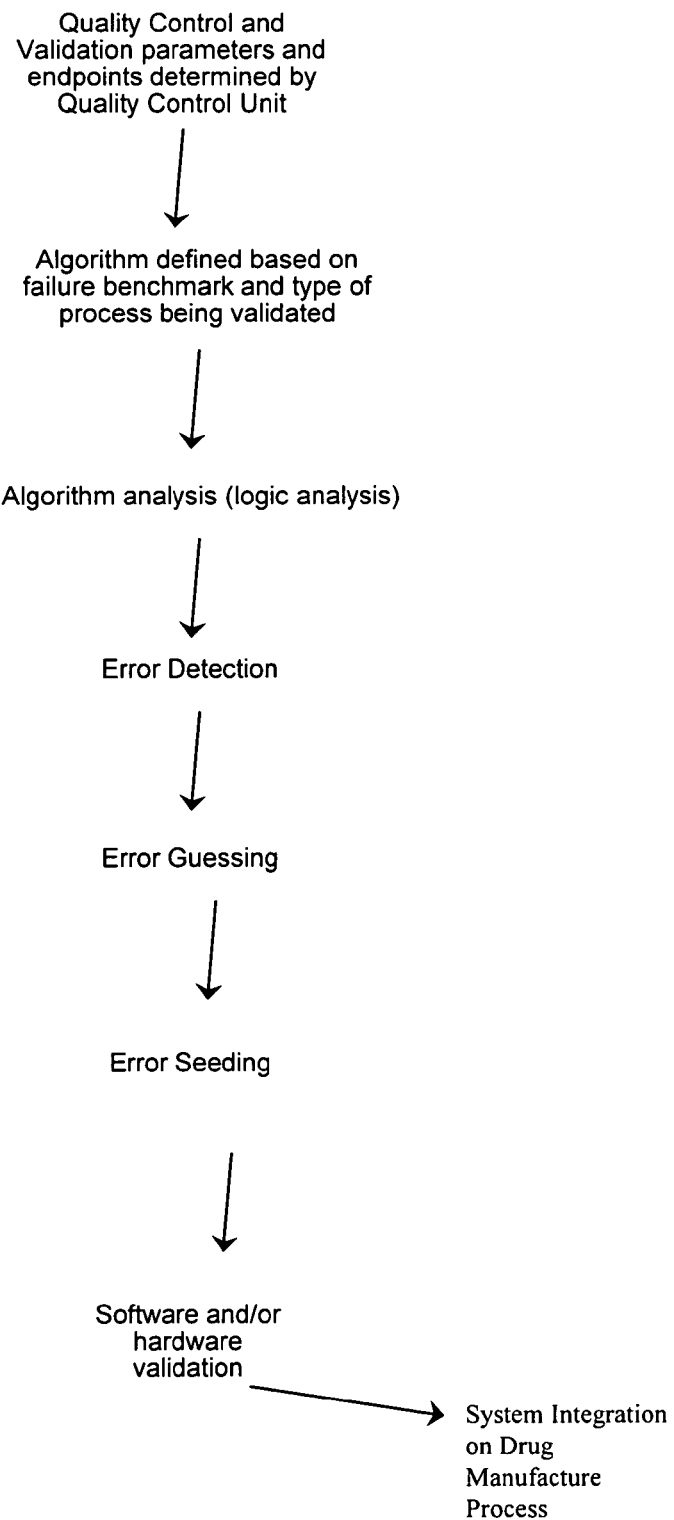
Figure 3: Schematic of Failure Analysis Method

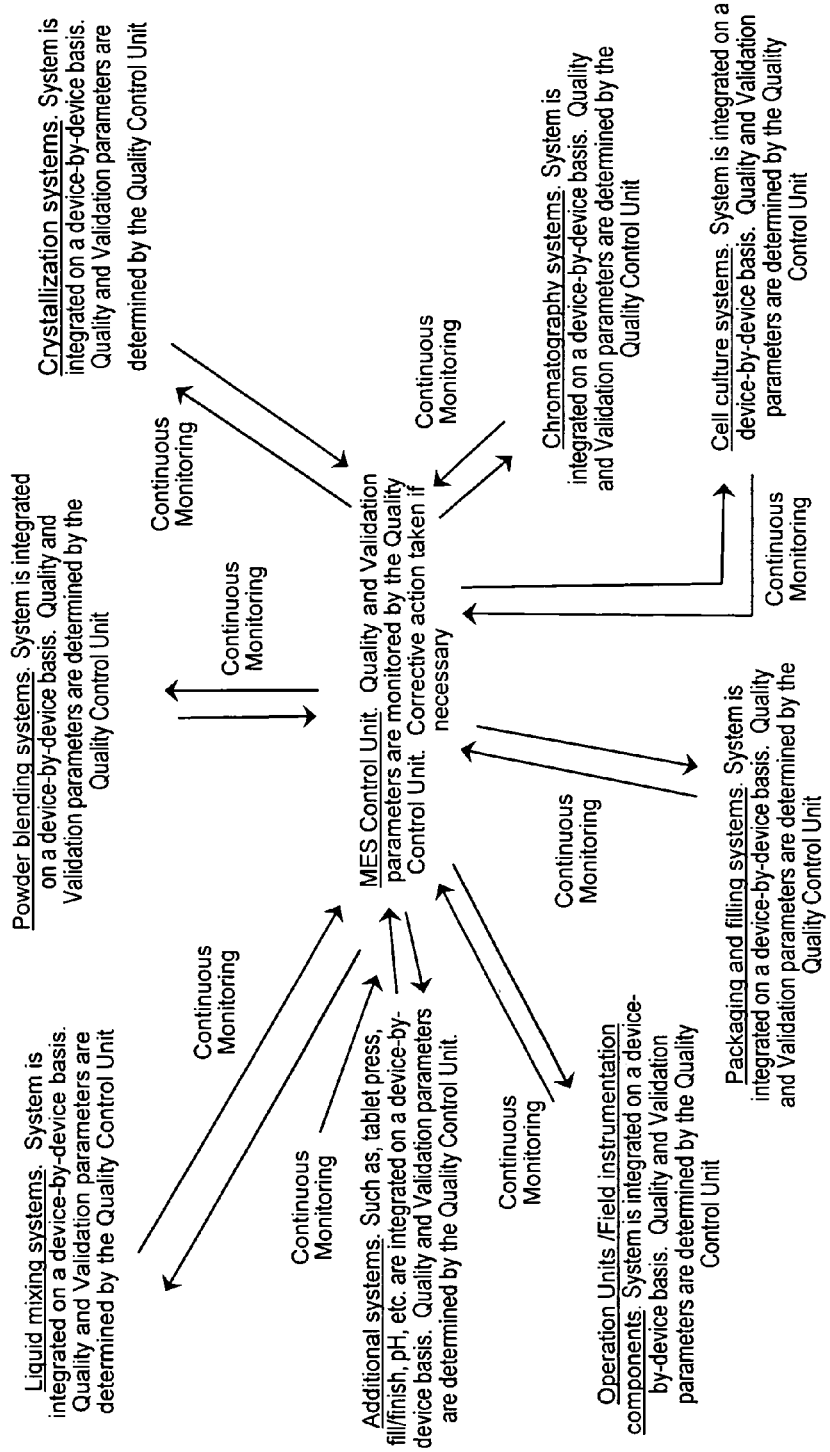
Figure 4: Schematic of Manufacturing Execution System Integration

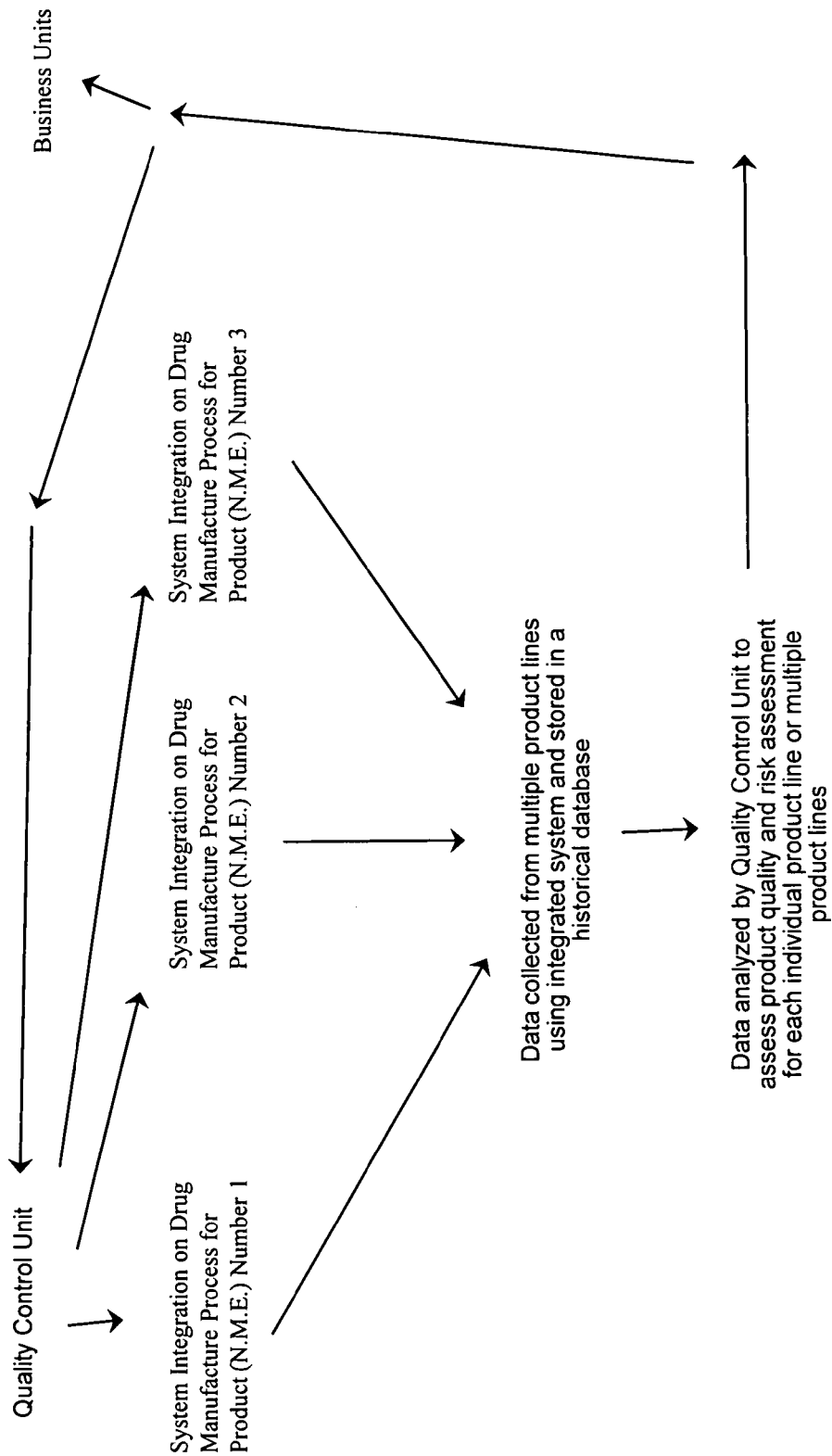

MONITORING ACCEPTANCE CRITERIA OF PHARMACEUTICAL MANUFACTURING PROCESSES

CROSS-REFERENCE TO RELATED APPLICATIONS

This application is a continuation of U.S. Ser. No. 12/799,097 filed 15 Apr. 2010, which is a continuation of U.S. Ser. No. 11/503,767 filed 14 Aug. 2006, now U.S. Pat. No. 7,799,273 issued on 21 Sep. 2010, which is a continuation-in-part of U.S. Ser. No. 11/500,642, filed 8 Aug. 2006, now U.S. Pat. No. 7,471,991 issued on 30 Dec. 2008, which is a continuation of U.S. Ser. No. 10/840,732, filed 6 May 2004, now U.S. Pat. No. 7,444,197 issued on 28 Oct. 2008. The contents of which are fully incorporated by reference.

STATEMENT OF RIGHTS TO INVENTIONS MADE UNDER FEDERALLY SPONSORED RESEARCH

Not applicable.

FIELD OF THE INVENTION

The invention described herein relates to methods, systems, and software program that are modified for use in software and hardware validation, quality and risk assessment, and monitoring of pharmaceutical manufacturing processes. The invention further relates to the enhancement of quality assurance implementation protocols and process analytical technology in current good manufacturing practice in manufacturing, processing, packing, and/or holding of drugs.

BACKGROUND OF THE INVENTION

Over the last two decades, significant changes in the environment of pharmaceutical regulation have occurred and have resulted in incremental adjustments in regulatory approaches to product quality. These changes included an increased number of pharmaceutical products and a greater role of medicines in health care, decreased frequency of manufacturing inspections as a result of fewer resources available for pharmaceutical manufacturing inspections, accumulation of experience with, "and lessons learned from", various approaches to the regulation of product quality, advances in the pharmaceutical sciences and manufacturing technologies, application of biotechnology in drug discovery and manufacturing, advances in the science and management of quality and, globalization of the pharmaceutical industry. The cumulative impact of these changes has been greater than the sum of the parts and there is an industry wide need to develop integrated approaches to monitor and assess the validation of processes and overall quality of products provided to end users and patients.

Looking ahead the most up-to-date concepts of risk management and quality systems approaches should be incorporated while continuing to ensure product quality. The latest scientific advances in pharmaceutical manufacturing and technology are encouraged. Additionally, the submission review program and the inspection program should operate in a coordinated and synergistic manner and regulation and manufacturing standards should be applied consistently. The management of validation and quality assurance programs should encourage innovation in the pharmaceutical manufacturing sector in order to provide the most effective public health protection. Resource limitations prevent uniformly intensive coverage of all pharmaceutical products and production. Significant advances in the pharmaceutical sciences and in manufacturing technologies have occurred over the last two decades. While this knowledge has been incorporated in an ongoing manner into product quality regulation, the fundamental nature of the changes dictates a thorough evaluation of the science base to ensure that product quality assurance and validation not only incorporates up-to-date science, but also encourages further advances in technology. Integrated quality systems orientation principles from various innovative approaches to manufacturing quality that have been developed in the past decade should be evaluated for applicability and cGMP requirements and related pre-approval requirements should be evaluated according to applicable principles. In addition, interaction of the pre-market CMC review process and the application of cGMP requirements should be evaluated as an integrated system.

With the globalization of pharmaceutical manufacturing requires a global approach to integration keeping in mind the overall objective of strong public health protection. To accomplish these needed goals there is a need to carry out the following actions. The artisan should use emerging science and data analysis to enhance validation and quality assurance programs to target the highest risk areas. From the aforementioned, the evaluation of the feasibility of establishing dedicated and integrated cadres of pharmaceutical validation and quality assurance experts should become readily apparent to one of ordinary skill in the art. Also apparent to one of ordinary skill in the art is the ability to provide a cost-efficient network of validation and quality assurance protocols. By providing an integrated and user-friendly approach to validation and quality assurance the overall benefit to the public at-large is pharmaceutical end products available at lower costs. This is turn will allow more persons or animals to benefit from innovations that occur in the treatment of disease. Additionally, there is also a need to use these modalities as research tools to monitor, assess, and further the state of the art in all areas of life science treatment and studies, specifically biotechnology and pharmaceuticals.

SUMMARY OF THE INVENTION

The invention provides for a software program that validates devices used in the manufacture, processing, and storing of drugs. As used herein, the term "drug" is synonymous with "pharmaceutical". In certain embodiments, the program can be modified to conform to the programming language and operating system requirements of an individual system. In a further embodiment, the program is used to validate hardware used in drug manufacture. In another embodiment, the program is used to validate software used in drug manufacture. In another embodiment, the program is used to monitor quality assurance protocols put in place by the quality control unit.

The invention further provides methods for validating drug manufacture using the application software. In one embodiment, the method comprises installation during the concept phase of manufacturing. In another embodiment, the method comprises installation at which time the manufacture process is on-line. In another embodiment, the method comprises installation during the course of quality assurance. In another embodiment, the method comprises monitoring the validation and quality assurance based on a routine maintenance schedule.

The invention further comprises a system which integrates application software and methods disclosed herein to provide a comprehensive validation and quality assurance protocol that is used by a plurality of end users whereby the data compiled from the system is analyzed and used to determine is quality assurance protocols and validation protocols are being achieved.

The invention further comprises an improvement to previously disclosed embodiments. The improvement comprises implementing the methods, system, and software program to multiple product lines whereby simultaneous production lines are monitored using the same system.

The invention further comprises implementation of the methods described herein into the crystallization process subset of the pharmaceutical manufacturing process whereby the data compiled by the crystallization process is tracked continuously overtime and said data is used to analyze the crystallization process and whereby said data is integrated and used to analyze the quality control process of the pharmaceutical manufacturing process at-large.

The invention further comprises implementation of the methods described herein into the tablet press process subset of the pharmaceutical manufacturing process whereby the data compiled by the tablet press process is tracked continuously overtime and said data is used to analyze the tablet press process and whereby said data is integrated and used to analyze the quality control process of the pharmaceutical manufacturing process at-large.

The invention further comprises implementation of the methods described herein into the chromatography process subset of the pharmaceutical manufacturing process whereby the data compiled by the chromatography process is tracked continuously overtime and said data is used to analyze the chromatography process and whereby said data is integrated and used to analyze the quality control process of the pharmaceutical manufacturing process at-large.

The invention further comprises implementation of the methods described herein into the pH monitoring process subset of the pharmaceutical manufacturing process whereby the data compiled by the pH monitoring process is tracked continuously overtime and said data is used to analyze the pH monitoring process and whereby said data is integrated and used to analyze the quality control process of the pharmaceutical manufacturing process at-large.

The invention further comprises implementation of the methods described herein into the liquid mixing process subset of the pharmaceutical manufacturing process whereby the data compiled by the liquid mixing process is tracked continuously overtime and said data is used to analyze the liquid mixing process and whereby said data is integrated and used to analyze the quality control process of the pharmaceutical manufacturing process at-large.

The invention further comprises implementation of the methods described herein into the powder blending process subset of the pharmaceutical manufacturing process whereby the data compiled by the powder blending process is tracked continuously overtime and said data is used to analyze the powder blending process and whereby said data is integrated and used to analyze the quality control process of the pharmaceutical manufacturing process at-large.

The invention further comprises implementation of the methods described herein into the Water-for-injection system of the pharmaceutical manufacturing process whereby the data compiled by the Water-for-injection system is tracked continuously overtime and said data is used to analyze the Water-for-injection system and whereby said data is integrated and used to analyze the quality control process of the pharmaceutical manufacturing process at-large.

The invention further comprises implementation of the methods described herein into the water purification and pre-treatment system of the pharmaceutical manufacturing process whereby the data compiled by the water purification and pre-treatment system is tracked continuously overtime and said data is used to analyze the Water-for-injection system and whereby said data is integrated and used to analyze the quality control process of the pharmaceutical manufacturing process at-large.

The invention further comprises implementation of the methods described herein into the finishing and packaging process subset of the pharmaceutical manufacturing process whereby the data compiled by the finishing and packaging process is tracked continuously overtime and said data is used to analyze the finishing and packaging process and whereby said data is integrated and used to analyze the quality control process of the pharmaceutical manufacturing process at-large.

The invention further comprises implementation of the methods described herein into the operational unit(s) utilized during the pharmaceutical manufacturing process whereby the data compiled by the operational unit(s) is tracked continuously overtime and said data is used to analyze the operational unit(s) and whereby said data is integrated and used to analyze the quality control process of the pharmaceutical manufacturing process at-large. For the purposes described herein, "operational unit(s)" includes but is not limited to, motors, drives, compressed air systems, HVAC, Boilers, and back-up generators. In one embodiment, the methods described herein are integrated into one operational unit. However, one of ordinary skill in the art will appreciate that integration into every operational unit will be preferred.

The invention further comprises implementation of the methods described herein into the field instrumentation component(s) utilized during the pharmaceutical manufacturing process whereby the data compiled by the field instrumentation component(s) is tracked continuously overtime and said data is used to analyze the field instrumentation component(s) and whereby said data is integrated and used to analyze the quality control process of the pharmaceutical manufacturing process at-large. For the purposes described herein "field instrumentation component(s)" includes but is not limited to, calibration tools, flow meters, intrinsic safety devices, leveling components, weighting components, process analyzers, thermometers, and valves. In one embodiment, the methods described herein are integrated into one field instrumentation component. However, one of ordinary skill in the art will appreciate that integration into every field instrumentation component will be preferred.

The invention further comprises implementation of the methods described herein into the batch optimization of cell culture systems of the pharmaceutical manufacturing process whereby the data compiled by the cell culture system is tracked continuously overtime and said data is used to analyze the cell culture system and whereby said data is integrated and used to analyze the quality control process of the pharmaceutical manufacturing process at-large.

The invention further comprises implementation of the methods described herein into the outsourced process of the pharmaceutical manufacturing process whereby the data compiled by the outsourced process is tracked continuously overtime and said data is used to analyze the outsourced process and whereby said data is integrated and used to analyze the quality control process of the pharmaceutical manufacturing process at-large. For the purposes described herein, "outsourced process" includes but is not limited to, processes that are ancillary to the pharmaceutical manufacturing process such as fill and finish that are performed off-site. In a preferred embodiment, the methods described herein are integrated between the sponsor manufacturer and a plurality of subcontractors.

The invention further comprises a manufacturing execution system, which controls the pharmaceutical manufacturing process and increases productivity and improve's quality of pharmaceuticals.

BRIEF DESCRIPTION OF THE FIGURES

FIG. 1. Schematic of analysis method.

FIG. 2. Flowchart of Standard Hazard Analysis and Mitigation.

FIG. 3. Schematic of failure analysis method.

FIG. 4. Schematic of manufacturing execution system. As shown in FIG. 4, each process in the pharmaceutical manufacturing system is integrated with a computer product and data is monitored assessing various factors, the parameters of which are set forth by the quality control unit. The specific systems are then cumulatively integrated by the quality control unit and a data record is made. The data record is maintained and used to determine risk factors and make quality assessments.

FIG. 5. Schematic of integrating the method and software into multiple product lines. As shown in FIG. 5, the quality control unit monitors the entire manufacturing execution system for several products. Data for each step is monitored to provide a quality assessment for each step as well as for the process at-large. The method is repeated on a MES for a plurality of products. When the MES for each product contains an identical process, the data from each product line is integrated and monitored to provide a safety and quality assessment. Over time the processes become more predictable and as a result the risk readily maintained. Data is returned to the Quality Control Unit or forward to the business units for analysis.

DETAILED DESCRIPTION OF THE INVENTION

Outline of Sections

I.) Definitions
II.) Software Program
III.) Analysis
IV.) KITS/Articles of Manufacture I.) Definitions Unless otherwise defined, all terms of art, notations and other scientific terms or terminology used herein are intended to have the meanings commonly understood by those of skill in the art to which this invention pertains unless the context clearly indicates otherwise. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art, such as, for example, the widely utilized current Good Manufacturing Practice guidelines.

As used herein the terms "drug" and "pharmaceutical" include veterinary drugs and human drugs, including human biological drug products.

"abstraction" means the separation of the logical properties of data or function from its implementation in a computer program.

"access time" means the time interval between the instant at which a call for data is initiated and the instant at which the delivery of the data is completed.

"adaptive maintenance" means software maintenance performed to make a computer program usable in a changed environment.

"algorithm" means any sequence of operations for performing a specific task.

"algorithm analysis" means a software verification and validation ("V&V") task to ensure that the algorithms selected are correct, appropriate, and stable, and meet all accuracy, timing, and sizing requirements.

"analog" means pertaining to data [signals] in the form of continuously variable [wave form] physical quantities; e.g., pressure, resistance, rotation, temperature, voltage.

"analog device" means a device that operates with variables represented by continuously measured quantities such as pressures, resistances, rotations, temperatures, and voltages.

"analog-to-digital converter" means input related devices which translate an input device's [sensor] analog signals to the corresponding digital signals needed by the computer.

"analysis" means a course of reasoning showing that a certain result is a consequence of assumed premises.

"application software" means software designed to fill specific needs of a user.

"bar code" means a code representing characters by sets of parallel bars of varying thickness and separation that are read optically by transverse scanning.

"basic input/output system" means firmware that activates peripheral devices in a PC. Includes routines for the keyboard, screen, disk, parallel port and serial port, and for internal services such as time and date. It accepts requests from the device drivers in the operating system as well from application programs. It also contains autostart functions that test the system on startup and prepare the computer for operation. It loads the operating system and passes control to it.

"batch processing" means execution of programs serially with no interactive processing.

"benchmark" means a standard against which measurements or comparisons can be made.

"block" means a string of records, words, or characters that for technical or logical purposes are treated as a unity.

"block check" means the part of the error control procedure that is used for determining that a block of data is structured according to given rules.

"block diagram" means a diagram of a system, instrument or computer, in which the principal parts are represented by suitably annotated geometrical figures to show both the basic functions of the parts and the functional relationships between them.

"blueprint" means a detailed plan or outline.

"boot" means to initialize a computer system by clearing memory and reloading the operating system. A distinction can be made between a warm boot and a cold boot. A cold boot means starting the system from a powered-down state. A warm boot means restarting the computer while it is powered-up. Important differences between the two procedures are; 1) a power-up self-test, in which various portions of the hardware [such as memory] are tested for proper operation, is performed during a cold boot while a warm boot does not normally perform such self-tests, and 2) a warm boot does not clear all memory.

"bootstrap" means a short computer program that is permanently resident or easily loaded into a computer and whose execution brings a larger program, such an operating system or its loader, into memory.

"boundary value" means a data value that corresponds to a minimum or maximum input, internal, or output value specified for a system or component.

"boundary value analysis" means a selection technique in which test data are chosen to lie along "boundaries" of the input domain [or output range] classes, data structures, procedure parameters, etc.

"branch analysis" means a test case identification technique which produces enough test cases such that each decision has a true and a false outcome at least once.

"calibration" means ensuring continuous adequate performance of sensing, measurement, and actuating equipment with regard to specified accuracy and precision requirements.

"certification" means technical evaluation, made as part of and in support of the accreditation process, that establishes the extent to which a particular computer system or network design and implementation meet a pre-specified set of requirements.

"change control" means the processes, authorities for, and procedures to be used for all changes that are made to the computerized system and/or the system's data. Change control is a vital subset of the Quality Assurance [QA] program within an establishment and should be clearly described in the establishment's SOPs.

"check summation" means a technique for error detection to ensure that data or program files have been accurately copied or transferred.

"compiler" means computer program that translates programs expressed in a high-level language into their machine language equivalents.

"computer system audit" means an examination of the procedures used in a computer system to evaluate their effectiveness and correctness and to recommend improvements.

"computer system security" means the protection of computer hardware and software from accidental or malicious access, use, modification, destruction, or disclosure.

"concept phase" means the initial phase of a software development project, in which user needs are described and evaluated through documentation.

"configurable, off-the-shelf software" means application software, sometimes general purpose, written for a variety of industries or users in a manner that permits users to modify the program to meet their individual needs.

"control flow analysis" means a software V&V task to ensure that the proposed control flow is free of problems, such as design or code elements that are unreachable or incorrect.

"controller" means hardware that controls peripheral devices such as a disk or display screen. It performs the physical data transfers between main memory and the peripheral device.

"conversational" means pertaining to a interactive system or mode of operation in which the interaction between the user and the system resembles a human dialog.

"coroutine" means a routine that begins execution at the point at which operation was last suspended, and that is not required to return control to the program or subprogram that called it.

"corrective maintenance" means maintenance performed to correct faults in hardware or software.

"critical control point" means a function or an area in a manufacturing process or procedure, the failure of which, or loss of control over, may have an adverse affect on the quality of the finished product and may result in an unacceptable health risk.

"data analysis" means evaluation of the description and intended use of each data item in the software design to ensure the structure and intended use will not result in a hazard. Data structures are assessed for data dependencies that circumvent isolation, partitioning, data aliasing, and fault containment issues affecting safety, and the control or mitigation of hazards.

"data integrity" means the degree to which a collection of data is complete, consistent, and accurate.

"data validation" means a process used to determine if data are inaccurate, incomplete, or unreasonable. The process may include format checks, completeness checks, check key tests, reasonableness checks and limit checks.

"design level" means the design decomposition of the software item; e.g., system, subsystem, program or module.

"design phase" means the period of time in the software life cycle during which the designs for architecture, software components, interfaces, and data are created, documented, and verified to satisfy requirements.

"diagnostic" means pertaining to the detection and isolation of faults or failures.

"different software system analysis" means Analysis of the allocation of software requirements to separate computer systems to reduce integration and interface errors related to safety. Performed when more than one software system is being integrated.

"dynamic analysis" means analysis that is performed by executing the program code.

"encapsulation" means a software development technique that consists of isolating a system function or a set of data and the operations on those data within a module and providing precise specifications for the module.

"end user" means a person, device, program, or computer system that uses an information system for the purpose of data processing in information exchange.

"error detection" means techniques used to identify errors in data transfers.

"error guessing" means the selection criterion is to pick values that seem likely to cause errors.

"error seeding" means the process of intentionally adding known faults to those already in a computer program for the purpose of monitoring the rate of detection and removal, and estimating the number of faults remaining in the program.

"failure analysis" means determining the exact nature and location of a program error in order to fix the error, to identify and fix other similar errors, and to initiate corrective action to prevent future occurrences of this type of error.

"Failure Modes and Effects Analysis" means a method of reliability analysis intended to identify failures, at the basic component level, which have significant consequences affecting the system performance in the application considered.

"FORTRAN" means an acronym for FORmula TRANslator, the first widely used high-level programming language. Intended primarily for use in solving technical problems in mathematics, engineering, and science.

"life cycle methodology" means the use of any one of several structured methods to plan, design, implement, test and operate a system from its conception to the termination of its use.

"logic analysis" means evaluates the safety-critical equations, algorithms, and control logic of the software design.

"low-level language" means the advantage of assembly language is that it provides bit-level control of the processor allowing tuning of the program for optimal speed and performance. For time critical operations, assembly language may be necessary in order to generate code which executes fast enough for the required operations.

"maintenance" means activities such as adjusting, cleaning, modifying, overhauling equipment to assure performance in accordance with requirements.

"modulate" means varying the characteristics of a wave in accordance with another wave or signal, usually to make user equipment signals compatible with communication facilities.

"Pascal" means a high-level programming language designed to encourage structured programming practices.

"path analysis" means analysis of a computer program to identify all possible paths through the program, to detect incomplete paths, or to discover portions of the program that are not on any path.

"quality assurance" means the planned systematic activities necessary to ensure that a component, module, or system conforms to established technical requirements.

"quality control" means the operational techniques and procedures used to achieve quality requirements.

"software engineering" means the application of a systematic, disciplined, quantifiable approach to the development, operation, and maintenance of software.

"software engineering environment" means the hardware, software, and firmware used to perform a software engineering effort.

"software hazard analysis" means the identification of safety-critical software, the classification and estimation of potential hazards, and identification of program path analysis to identify hazardous combinations of internal and environmental program conditions.

"software reliability" means the probability that software will not cause the failure of a system for a specified time under specified conditions.

"software review" means an evaluation of software elements to ascertain discrepancies from planned results and to recommend improvement.

"software safety change analysis" means analysis of the safety-critical design elements affected directly or indirectly by the change to show the change does not create a new hazard, does not impact on a previously resolved hazard, does not make a currently existing hazard more severe, and does not adversely affect any safety-critical software design element.

"software safety code analysis" means verification that the safety-critical portions of the design are correctly implemented in the code.

"software safety design analysis" means verification that the safety-critical portion of the software design correctly implements the safety-critical requirements and introduces no new hazards.

"software safety requirements analysis" means analysis evaluating software and interface requirements to identify errors and deficiencies that could contribute to a hazard.

"software safety test analysis" means analysis demonstrating that safety requirements have been correctly implemented and that the software functions safely within its specified environment.

"system administrator" means the person that is charged with the overall administration, and operation of a computer system. The System Administrator is normally an employee or a member of the establishment.

"system analysis" means a systematic investigation of a real or planned system to determine the functions of the system and how they relate to each other and to any other system.

"system design" means a process of defining the hardware and software architecture, components, modules, interfaces, and data for a system to satisfy specified requirements.

"top-down design" means pertaining to design methodology that starts with the highest level of abstraction and proceeds through progressively lower levels.

"traceability analysis" means the tracing of Software Requirements Specifications requirements to system requirements in concept documentation.

"validation" means establishing documented evidence which provides a high degree of assurance that a specific process will consistently produce a product meeting its predetermined specifications and quality attributes.

"validation, process" means establishing documented evidence which provides a high degree of assurance that a specific process will consistently produce a product meeting its predetermined specifications and quality characteristics.

"validation, prospective" means validation conducted prior to the distribution of either a new product, or product made under a revised manufacturing process, where the revisions may affect the product's characteristics.

"validation protocol" means a written plan stating how validation will be conducted, including test parameters, product characteristics, production equipment, and decision points on what constitutes acceptable test results.

"validation, retrospective" means validation of a process for a product already in distribution based upon accumulated production, testing and control data. Retrospective validation can also be useful to augment initial premarket prospective validation for new products or changed processes. Test data is useful only if the methods and results are adequately specific. Whenever test data are used to demonstrate conformance to specifications, it is important that the test methodology be qualified to assure that the test results are objective and accurate.

"validation, software" means. determination of the correctness of the final program or software produced from a development project with respect to the user needs and requirements. Validation is usually accomplished by verifying each stage of the software development life cycle.

"structured query language" means a language used to interrogate and process data in a relational database. Originally developed for IBM mainframes, there have been many implementations created for mini and micro computer database applications. SQL commands can be used to interactively work with a data base or can be embedded with a programming language to interface with a database.

"Batch" means a specific quantity of a drug or other material that is intended to have uniform character and quality, within specified limits, and is produced according to a single manufacturing order during the same cycle of manufacture.

"Component" means any ingredient intended for use in the manufacture of a drug product, including those that may not appear in such drug product.

"Drug product" means a finished dosage form, for example, tablet, capsule, solution, etc., that contains an active drug ingredient generally, but not necessarily, in association with inactive ingredients. The term also includes a finished dosage form that does not contain an active ingredient but is intended to be used as a placebo.

"Active ingredient" means any component that is intended to furnish pharmacological activity or other direct effect in the diagnosis, cure, mitigation, treatment, or prevention of disease, or to affect the structure or any function of the body of man or other animals. The term includes those components that may undergo chemical change in the manufacture of the drug product and be present in the drug product in a modified form intended to furnish the specified activity or effect.

"Inactive ingredient" means any component other than an active ingredient.

"In-process material" means any material fabricated, compounded, blended, or derived by chemical reaction that is produced for, and used in, the preparation of the drug product.

"Lot number, control number, or batch number" means any distinctive combination of letters, numbers, or symbols, or any combination thereof, from which the complete history of the manufacture, processing, packing, holding, and distribution of a batch or lot of drug product or other material can be determined.

"Quality control unit" means any person or organizational element designated by the firm to be responsible for the duties relating to quality control.

"Acceptance criteria" means the product specifications and acceptance/rejection criteria, such as acceptable quality level and unacceptable quality level, with an associated sampling plan, that are necessary for making a decision to accept or reject a lot or batch.

"Manufacturing execution system" (a.k.a. MES) means an integrated hardware and software solution designed to measure and control activities in the production areas of manufacturing organizations to increase productivity and improve quality.

"Process analytical technology" (a.k.a. PAT) means a mechanism to design, analyze, and control pharmaceutical manufacturing processes through the measurement of critical process parameters and quality attributes.

"New molecular entity" (a.k.a. NME or New Chemical Entity ("CNE")) means a drug that contains no active moiety that has been approved by FDA. An active moiety means the molecule or ion, excluding those appended portions of the molecule that cause the drug to be an ester, salt (including a salt with hydrogen or coordination bonds), or other noncovalent derivative (such as a complex, chelate, or clathrate) of the molecule, responsible for the physiological or pharmacological action of the drug substance.

"Crystallization process" means the natural or artificial process of formation of solid crystals from a homogeneous solution consisting of two (2) major steps, (i) nucleazation and (ii) crystal growth.

"Tablet press" means the apparatus or machine which compresses powder into a tablet by the action of one upper and one lower punch sliding along closing cam tracks and meeting together at a predetermined point in a die between the two main pressure rolls.

"Chromatography" means collectively a family of laboratory techniques for the separation of mixtures. It involves passing a mixture which contains the analyte through a stationary phase, which separates it from other molecules in the mixture and allows it to be isolated.

"pH" means is a measure of the activity of hydrogen ions ($H^+$) in a solution and, therefore, its acidity.

II.) Software Program (Computer Product)

The invention provides for a software program that is programmed in a high-level or low-level programming language, preferably a relational language such as structured query language which allows the program to interface with an already existing program or a database. Preferably, however, the program will be initiated in parallel with the manufacturing process or quality assurance ("QA") protocol. This will allow the ability to monitor the manufacturing and QA process from its inception. However, in some instances the program can be bootstrapped into an already existing program that will allow monitoring from the time of execution (i.e. bootstrapped to configurable off-the-shelf software).

It will be readily apparent to one of skill in the art that the preferred embodiment will be a software program that can be easily modified to conform to numerous software-engineering environments. One of ordinary skill in the art will understand and will be enabled to utilize the advantages of the invention by designing the system with top-down design. The level of abstraction necessary to achieve the desired result will be a direct function of the level of complexity of the process that is being monitored. For example, the critical control point for monitoring an active ingredient versus an inactive ingredient may not be equivalent. Similarly, the critical control point for monitoring an in-process material may vary from component to component and often from batch to batch.

One of ordinary skill will appreciate that to maximize results the ability to amend the algorithm needed to conform to the validation and QA standards set forth by the quality control unit on each step during manufacture will be preferred. This differential approach to programming will provide the greatest level of data analysis leading to the highest standard of data integrity.

The preferred embodiments may be implemented as a method, system, or program using standard software programming and/or engineering techniques to produce software, firmware, hardware, or any combination thereof. The term "computer product" as used herein is intended to encompass one or more computer programs and data files accessible from one or more computer-readable devices, firmware, programmable logic, memory devices (e.g. EEPROM's, ROM's, PROM's, RAM's, SRAM's, etc.) hardware, electronic devices, a readable storage diskette, CD-ROM, a file server providing access to programs via a network transmission line, wireless transmission media, signals propagating through space, radio waves, infrared signals, etc. Those of skill in the art will recognize that many modifications may be made without departing from the scope of the present invention.

III.) Analysis

The invention provides for a method of analyzing data that is compiled as a result of the manufacturing of pharmaceuticals. Further the invention provides for the analysis of data that is compiled as a result of a QA program used to monitor the manufacture of drugs in order to maintain the highest level of data integrity. In one embodiment, the parameters of the data will be defined by the quality control unit. Generally, the quality control unit will provide endpoints that need to be achieved to conform to cGMP regulations or in some instances an internal endpoint that is more restrictive to the minimum levels that need to be achieved.

In a preferred embodiment, the invention provides for data analysis using boundary value analysis. The boundary value will be set forth by the quality control unit. Using the boundary values set forth for a particular phase of manufacture the algorithm is defined. Once the algorithm is defined, an algorithm analysis (i.e. logic analysis) takes place. One of skill in the art will appreciate that a wide variety of tools are used to confirm algorithm analysis such as an accuracy study processor.

One of ordinary skill will appreciate that different types of data will require different types of analysis. In a further embodiment, the program provides a method of analyzing block data via a block check. If the block check renders an affirmative analysis, the benchmark has been met and the analysis continues to the next component. If the block check renders a negative the data is flagged via standard recognition files known in the art and a hazard analysis and hazard mitigation occurs.

In a further embodiment, the invention provides for data analysis using branch analysis. The test cases will be set forth by the quality control unit.

In a further embodiment, the invention provides for data analysis using control flow analysis. The control flow analysis will calibrate the design level set forth by the quality control unit which is generated in the design phase.

In a further embodiment, the invention provides for data analysis using failure analysis. The failure analysis is initiated using the failure benchmark set forth by the quality control unit and then using standard techniques to come to error detection. The preferred technique will be top-down. For example, error guessing based on quality control group parameters which are confirmed by error seeding.

In a further embodiment, the invention provides for data analysis using path analysis. The path analysis will be initiated after the design phase and will be used to confirm the design level. On of ordinary skill in the art will appreciate that the path analysis will be a dynamic analysis depending on the complexity of the program modification. For example, the path analysis on the output of an end product will be inherently more complex that the path analysis for the validation of an in-process material. However, one of ordinary skill will understand that the analysis is the same, but the parameters set forth by the quality control unit will differ.

The invention provides for a top-down design to software analysis. This preferred embodiment is advantageous because the parameters of analysis will be fixed for any given process and will be set forth by the quality control unit. Thus, performing software safety code analysis then software safety design analysis, then software safety requirements analysis, and then software safety test analysis will be preferred.

The aforementioned analysis methods are used for several non-limiting embodiments, including but not limited to, validating QA software, validating pharmaceutical manufacturing, and validating process designs wherein the integration of the system design will allow for more efficient determination of acceptance criteria in a batch, in-process material, batch number, control number, and lot number and allow for increased access time thus achieving a more efficient cost-saving manufacturing process.

IV.) Kits/Articles of Manufacture

For use in basic input/output systems, hardware calibrations, software calibrations, computer systems audits, computer system security certification, data validation, different software system analysis, quality control, and the manufacturing of drug products described herein, kits are within the scope of the invention. Such kits can comprise a carrier, package, or container that is compartmentalized to receive one or more containers such as boxes, shrink wrap, and the like, each of the container(s) comprising one of the separate elements to be used in the method, along with a program or insert comprising instructions for use, such as a use described herein.

The kit of the invention will typically comprise the container described above and one or more other containers associated therewith that comprise materials desirable from a commercial and user standpoint, programs listing contents and/or instructions for use, and package inserts with instructions for use.

A program can be present on or with the container. Directions and or other information can also be included on an insert(s) or program(s) which is included with or on the kit. The program can be on or associated with the container.

The terms "kit" and "article of manufacture" can be used as synonyms.

The article of manufacture typically comprises at least one container and at least one program. The containers can be formed from a variety of materials such as glass, metal or plastic.

EXAMPLES

Various aspects of the invention are further described and illustrated by way of the several examples that follow, none of which is intended to limit the scope of the invention.

Example 1

Implementation in Clinical Manufacturing Process

In one embodiment, the invention comprises the validation and quality control of drug products manufactured during the clinical phase of development. Generally, A phase I human clinical trial is initiated to assess the safety of doses of a drug product candidate in connection with the treatment of a disease. In the study, the safety of single doses when utilized as therapy is assessed. The trial design includes delivery of single doses of a drug product candidate escalating from approximately about 25 mg/m$^2$ to about 275 mg/m$^2$ over the course of the treatment in accordance with a pre-defined schedule (i.e. parameters defined by quality control unit).

Patients are closely followed for one-week following each administration of the drug product candidate. In particular, patients are assessed for safety concerns (i.e. toxicity, fever, shaking, chills, the development of an immunogenic response to the material.) Standard tests and follow-up are utilized to monitor each of these safety concerns. Patients are also assessed for clinical outcome and particularly treatment of the disease being evaluated.

The drug product candidate is demonstrated to be safe and efficacious, Phase II trials confirm the efficacy and refine optimum dosing.

The drug product candidate is safe in connection with the above-discussed trial, a Phase II human clinical trial confirms the efficacy and optimum dosing for monotherapy. Such trial is accomplished, and entails the same safety and outcome analyses, to the above-described trial with the exception being that patients do not receive other forms of treatment concurrently with the receipt of doses of the drug product candidate.

Once again, as the therapy discussed above is safe within the safety criteria discussed above, a Phase III human clinical trial is initiated.

As previously set forth, the acceptance criteria of all components used in the drug product manufacture for the purposes of the clinical trial are determined by the quality control unit. The analysis of the software and hardware occurs using any of the methods disclosed herein. (See for example FIG. 1 and FIG. 3). The program monitors and processes the data and stores the data using standard methods. The data is provided to an end user or a plurality of end users for assessing the quality of the batch. Furthermore, the data is stored for comparative analysis to previous batches to provide a risk-based assessment in case of failure. Using the historical analysis will provide a more streamlined manufacturing approach and will provide cost-saving over time. In addition, the invention comprises monitoring the data from initial process, monitoring the data at the end process, and monitoring the data from a routine maintenance schedule to ensure the system maintain data integrity and validation standard predetermined by the quality control unit.

Example 2

Implementation in Post-Clinical Commercial Manufacturing Process

Provided the drug product candidate has been awarded regulatory approval and is manufactured for commercial use. The invention comprises a method for monitoring the acceptance criteria of all components used in the drug product manufacture. The analysis of the software and hardware occurs using any of the methods disclosed herein. (See for example FIG. 1 and FIG. 3). The program monitors and processes the data and stores the data using methods known in the art. The data is provided to an end user or a plurality of end users for assessing the quality of the batch. Furthermore, the data is stored for comparative analysis to previous batches to provide a risk-based assessment in case of failure. Using the historical analysis will provide a more streamlined manufacturing approach and will provide cost-saving over time. In addition, the invention comprises monitoring the data from initial process, monitoring the data at the end process, and monitoring the data from a routine maintenance schedule to ensure the system maintain data integrity and validation standard predetermined by the quality control unit.

Example 3

Integration of Program into Manufacturing Hardware System

The invention comprises the integration of the computer product into a manufacturing hardware system. In this context, the term "hardware" means any physical device used in the pharmaceutical manufacturing process including, but not limited to, blenders, bio-reactors, capping machines, chromatography/separation systems, chilled water/circulating, glycol, coldrooms, clean steam, clean-in-place (CIP), compressed air, D.I./R.O. watersystems, dry heat sterilizers/ovens, fermentation equipment/bio reactors, freezers, filling equipment, filtration/purification, HVAC: environmental controls, incubators/environmentally controlled chambers, labelers, lyophilizers/freeze, dryers, mixing tanks, modular cleanrooms, neutralization systems, plant steam and condensate, process tanks/pressure, vessels, refrigerators, separation/purification equipment, specialty gas, systems, steam generators/pure steam systems, steam sterilizers, stopper washers, solvent recovery systems, tower water systems, waste inactivation systems/"kill" systems, vial inspection systems, vial washers, water for injection (WFI) systems, pure water systems, washers (glass, tank, carboys, etc.).

It will be understood by one of skill in the art that the computer product integrates the hardware via generally understood devices in the art (i.e. attached to the analog device via an analog to digital converter).

The computer product is integrated into the manufacturing system on a device-by-device basis. As previously set forth, the acceptance criteria of all devices used in the drug product manufacture for the purposes of the manufacturing process are determined by the quality control unit. The analysis of the software and hardware occurs using any of the methods disclosed herein. (See for example FIG. 1 and FIG. 3). The program monitors and processes the data and stores the data using standard methods. The data is provided to an end user or a plurality of end users for assessing the quality of data generated by the device. Furthermore, the data is stored for comparative analysis to previous batches to provide a risk-based assessment in case of failure. Using the historical analysis will provide a more streamlined manufacturing approach and will provide cost-saving over time. In addition, the invention comprises monitoring the data from initial process, monitoring the data at the end process, and monitoring the data from a routine maintenance schedule to ensure the system maintain data integrity and validation standard predetermined by the quality control unit.

Example 4

Integration of Program into Manufacturing Software System

The invention comprises the integration of the computer product into a manufacturing software system. In this context, the term "software" means any device used in the pharmaceutical manufacturing process including, but not limited to user-independent audit trails, time-stamped audit trails, data security, confidentiality systems, limited authorized system access, electronic signatures, bar codes, dedicated systems, add-on systems, control files, Internet, LAN's, etc.

The computer product is integrated into the manufacturing system on a device-by-device basis. As previously set forth, the acceptance criteria of all devices used in the drug product manufacture for the purposes of the manufacturing process are determined by the quality control unit. The analysis of the software and hardware occurs using any of the methods disclosed herein. (See for example FIG. 1 and FIG. 3). The program monitors and processes the data and stores the data using standard methods. The data is provided to an end user or a plurality of end users for assessing the quality of data generated by the device. Furthermore, the data is stored for comparative analysis to previous batches to provide a risk-based assessment in case of failure. Using the historical analysis will provide a more streamlined manufacturing approach and will provide cost-saving over time. In addition, the invention comprises monitoring the data from initial process, monitoring the data at the end process, and monitoring the data from a routine maintenance schedule to ensure the system maintain data integrity and validation standard predetermined by the quality control unit.

Example 5

Integration of Program into Quality Assurance System

The invention comprises the integration of the computer product into a quality assurance system. In this context, the term "quality assurance" means the planned systematic activities necessary to ensure that a component, module, or system conforms to established technical requirements. A quality assurance system will compliment either of the systems set for in the examples entitled "Integration of program into manufacturing hardware system" or "Integration of program into manufacturing software system" to ensure data integrity and reliability from the data that is generated set forth in either of the examples entitled "Implementation in Clinical Manufacturing Process" or "Implementation in Post-Clinical Commercial Manufacturing Process".

The computer product is integrated into the manufacturing system on a device-by-device basis. As previously set forth, the acceptance criteria of all devices used in the drug product manufacture for the purposes of the manufacturing process are determined by the quality control unit. The analysis of the software and hardware occurs using any of the methods disclosed herein. (See for example FIG. 1 and FIG. 3). The program monitors and processes the data and stores the data using standard methods. The data is provided to an end user or a plurality of end users for assessing the quality of data generated by the device. Furthermore, the data is stored for comparative analysis to previous batches to provide a risk-based assessment in case of failure. Using the historical analysis will provide a more streamlined manufacturing approach and will provide cost-saving over time. In addition, the invention comprises monitoring the data from initial process, monitoring the data at the end process, and monitoring the data from a routine maintenance schedule to ensure the system maintain data integrity and validation standard predetermined by the quality control unit.

Example 6

Integration of Program and Methods into a Comprehensive Cost-Saving System

The invention comprises a program and method integrated into a comprehensive cost-saving pharmaceutical manufacturing system. A user, preferably a system administrator, logs onto the system via secure means (i.e. password or other security measures known in the art) and inputs the boundary values for a particular component of the drug manufacturing process. The input is at the initial stage, the end product state, or any predetermined interval in between that has been established for routine maintenance by the quality control unit. The data is generated using any one of the various analysis methods described herein (as previously stated the type of analysis used is functional to the device or protocol being monitored or evaluated). Subsequent to the data analysis, any modifications or corrective action to the manufacturing process is implemented. The data is then stored by standard methods known in the art. Scheduled analysis of the stored data is maintained to provide a preventative maintenance of the manufacturing process. Over time, costs are reduced due to the tracking of data and analysis of troubled areas and frequency of hazards that occur on any given device in the manufacturing process. The system is implemented on every device which plays a role in drug manufacturing. The data compiled from every device is analyzed using the methods described herein.

Example 7

Integration of Program and Methods into a Comprehensive Cost-Saving System Utilizing Multiple Product Lines The invention comprises a program and method integrated into a comprehensive cost-saving pharmaceutical manufacturing system involving multiple product lines. the system is integrated as described in Example 6 (e.g. Drug X). The system is integrated on a plurality of products (e.g. Drug Y, Drug Z, etc.). The data record is kept for each product and analyzed individually for that product. Process parameters that are identical for each product are cumulated to create a comprehensive database on the manufacturing system at-large. The system achieves greater process integrity and quality control as a result of the cumulation. The maximization of process integrity and quality provides for a cost-savings over time.

Example 8

Integration of Methods and Program into Crystallization System

Background:
Crystallization is a key component to the pharmaceutical manufacturing process. Additionally, a substantial number of the pharmaceuticals manufactured today consist of at least one crystallization step. Despite its significance, typical problems consist of unsuitable particle size distribution, impurity issues (incorrect polymorphs, etc.), inconsistent yield, etc. It is an object of this invention to remedy these deficiencies.
Integration:
In one embodiment, the computer product is integrated into the crystallization process system hardware. It will be understood by one of skill in the art that the computer product integrates the hardware via generally understood devices in the art (i.e. attached to the analog device via an analog to digital converter).

The computer product is integrated into the crystallization system on a device-by-device basis. As previously set forth, the acceptance criteria of all devices used in the drug product manufacture for the purposes of the crystallization process are determined by the quality control unit. The analysis of the software and hardware occurs using any of the methods disclosed herein. (See for example FIG. 1 and FIG. 3). The program monitors and processes the data and stores the data using standard methods. The data is provided to an end user or a plurality of end users for assessing the quality of data generated by the device. Furthermore, the data is stored for comparative analysis to previous batches to provide a risk-based assessment in case of failure. Using the historical analysis will provide a more streamlined crystallization process and will provide cost-saving over time. In addition, the invention comprises monitoring the data from initial process, monitoring the data at the end process, and monitoring the data from a routine maintenance schedule to ensure the system maintain data integrity and validation standard predetermined by the quality control unit.
MES:
In one embodiment, the monitoring and analysis of the crystallization systems achieves a step of integration into a manufacturing execution system whereby manufacturing productivity and product quality are increased. Costs are streamlined over time.

Example 9

Integration of Methods and Program into Tablet Press System

Background:
In tablet making, powder is actually compressed together by traditional means. The end results is a pre-set tablet thickness which varies for each particular product. An overload can occur when too much powder is compressed at one time. The invention disclosed herein can remedy this deficiency.
Integration:
In one embodiment, the computer product is integrated into the tablet press system hardware. It will be understood by one of skill in the art that the computer product integrates the hardware via generally understood devices in the art (i.e. attached to the analog device via an analog to digital converter).

The computer product is integrated into the tablet press system on a device-by-device basis. As previously set forth, the acceptance criteria of all devices used in the drug product manufacture for the purposes of the tablet press process are determined by the quality control unit. The analysis of the software and hardware occurs using any of the methods disclosed herein. (See for example FIG. 1 and FIG. 3). The program monitors and processes the data and stores the data using standard methods. The data is provided to an end user or a plurality of end users for assessing the quality of data generated by the device. Furthermore, the data is stored for comparative analysis to previous batches to provide a risk-based assessment in case of failure. Using the historical analysis will provide a more streamlined tablet press process and will monitor to ensure the tablet press set point is not overloaded or underloaded. In addition, the invention comprises monitoring the data from initial process, monitoring the data at the end process, and monitoring the data from a routine maintenance schedule to ensure the system maintain data integrity and validation standard predetermined by the quality control unit.

MES:

In one embodiment, the monitoring and analysis of the tablet press systems achieves a step of integration into a manufacturing execution system whereby manufacturing productivity and product quality are increased. Costs are streamlined over time.

Example 10

Integration of Methods and Program into Chromatography System

Background:

Traditional chromatography techniques are very archaic and inefficient. The need to process large quantities of protein due to larger upstream processes (e.g. cell cultures) has strained downstream chromatography systems. It is an object of the invention to remedy this deficiency.

Integration:

In one embodiment, the computer product is integrated into the chromatography system hardware. It will be understood by one of skill in the art that the computer product integrates the hardware via generally understood devices in the art (i.e. attached to the analog device via an analog to digital converter).

The computer product is integrated into the chromatography system on a device-by-device basis. As previously set forth, the acceptance criteria of all devices used in the drug product manufacture for the purposes of the chromatography process are determined by the quality control unit. The analysis of the software and hardware occurs using any of the methods disclosed herein. (See for example FIG. 1 and FIG. 3). The program monitors and processes the data and stores the data using standard methods. The data is provided to an end user or a plurality of end users for assessing the quality of data generated by the device. Furthermore, the data is stored for comparative analysis to previous batches to provide a risk-based assessment in case of failure. Using the historical analysis will provide a more streamlined chromatography process and will monitor to ensure the upstream processes are gauged not to overload the downstream processes. In addition, the invention comprises monitoring the data from initial process, monitoring the data at the end process, and monitoring the data from a routine maintenance schedule to ensure the system maintain data integrity and validation standard predetermined by the quality control unit.

MES:

In one embodiment, the monitoring and analysis of the chromatography systems achieves a step of integration into a manufacturing execution system whereby manufacturing productivity and product quality are increased. Costs are streamlined over time.

Example 11

Integration of Methods and Program into pH System

Background:

Current instrumentation for monitoring pH values in the pharmaceutical manufacturing process are lacking in fundamental areas. First, current systems cannot handle an intense pH range. Furthermore, most instruments used in pharmaceutical manufacture are finishing and packing, however many current manufacturing products are isolated from aqueous organic mixtures. In addition, pH is a critical processing parameter and must be monitored stringently. Thus, current means of monitoring pH are very time consuming and can cause substantial delays. It is an object of the present invention to remedy this deficiency.

Integration:

In one embodiment, the computer product is integrated into the pH system hardware. It will be understood by one of skill in the art that the computer product integrates the hardware via generally understood devices in the art (i.e. attached to the analog device via an analog to digital converter).

The computer product is integrated into the pH system on a device-by-device basis. As previously set forth, the acceptance criteria of all devices used in the drug product manufacture for the purposes of the pH process are determined by the quality control unit. The analysis of the software and hardware occurs using any of the methods disclosed herein. (See for example FIG. 1 and FIG. 3). The program monitors and processes the data and stores the data using standard methods. The data is provided to an end user or a plurality of end users for assessing the quality of data generated by the device. Furthermore, the data is stored for comparative analysis to previous batches to provide a risk-based assessment in case of failure. Using the historical analysis will provide a more streamlined pH process and will monitor to ensure the pH is within the predetermined parameters. In addition, the invention comprises monitoring the data from initial process, monitoring the data at the end process, and monitoring the data from a routine maintenance schedule to ensure the system maintain data integrity and validation standard predetermined by the quality control unit.

MES:

In one embodiment, the monitoring and analysis of the pH systems achieves a step of integration into a manufacturing execution system whereby manufacturing productivity and product quality are increased. Costs are streamlined over time.

Example 12

Integration of Methods and Program into Liquid Mixing System

Background:

At first glance, liquid mixing and blending would seem very straightforward. One of ordinary skill in the art will appreciate the complexities associated with liquid mixing in the pharmaceutical manufacturing process. For example, mixing dissimilar liquids such as oil and water or mixing chemicals that harden are problems encountered on a daily basis. An object of the invention is to remedy these deficiencies.
Integration:

In one embodiment, the computer product is integrated into the liquid mixing system hardware. It will be understood by one of skill in the art that the computer product integrates the hardware via generally understood devices in the art (i.e. attached to the analog device via an analog to digital converter).

The computer product is integrated into the liquid mixing system on a device-by-device basis. As previously set forth, the acceptance criteria of all devices used in the drug product manufacture for the purposes of the liquid mixing process are determined by the quality control unit. The analysis of the software and hardware occurs using any of the methods disclosed herein. (See for example FIG. 1 and FIG. 3). The program monitors and processes the data and stores the data using standard methods. The data is provided to an end user or a plurality of end users for assessing the quality of data generated by the device. Furthermore, the data is stored for comparative analysis to previous batches to provide a risk-based assessment in case of failure. Using the historical analysis will provide a more streamlined liquid mixing process and will monitor to ensure that ingredients are mixed properly. In addition, the invention comprises monitoring the data from initial process, monitoring the data at the end process, and monitoring the data from a routine maintenance schedule to ensure the system maintain data integrity and validation standard predetermined by the quality control unit.
MES:

In one embodiment, the monitoring and analysis of the liquid mixing systems achieves a step of integration into a manufacturing execution system whereby manufacturing productivity and product quality are increased. Costs are streamlined over time.

Example 13

Integration of Methods and Program into Powder Blending System

Background:

Dry powder blending is one of the most widely used techniques in pharmaceutical manufacturing. One of skill in the art will appreciate that agitating a batch may not result in a homogeneous blend. Moreover, uniform blending may cause the ingredients to separate into layers. It is an object of the present invention to remedy these deficiencies.
Integration:

In one embodiment, the computer product is integrated into the powder blending system hardware. It will be understood by one of skill in the art that the computer product integrates the hardware via generally understood devices in the art (i.e. attached to the analog device via an analog to digital converter).

The computer product is integrated into the powder blending system on a device-by-device basis. As previously set forth, the acceptance criteria of all devices used in the drug product manufacture for the purposes of the powder blending process are determined by the quality control unit. The analysis of the software and hardware occurs using any of the methods disclosed herein. (See for example FIG. 1 and FIG. 3). The program monitors and processes the data and stores the data using standard methods. The data is provided to an end user or a plurality of end users for assessing the quality of data generated by the device. Furthermore, the data is stored for comparative analysis to previous batches to provide a risk-based assessment in case of failure. Using the historical analysis will provide a more streamlined powder blending process and will monitor to ensure that ingredients are mixed properly. In addition, the invention comprises monitoring the data from initial process, monitoring the data at the end process, and monitoring the data from a routine maintenance schedule to ensure the system maintain data integrity and validation standard predetermined by the quality control unit.
MES:

In one embodiment, the monitoring and analysis of the powder blending systems achieves a step of integration into a manufacturing execution system whereby manufacturing productivity and product quality are increased. Costs are streamlined over time.

Example 14

Integration of Methods and Program into Water-Based System

Background:

Water-based systems are used extensively in pharmaceutical manufacturing processes. From water purification to WFI systems to water treatment and disposal systems, the quality of the water used in the pharmaceutical manufacturing process is continuously monitored. One of skill in the art will appreciate the need to have ready access to water quality data and the need to monitor this data continuously. An object of the present invention is to achieve this matter.
Integration:

In one embodiment, the computer product is integrated into the water-based system hardware. It will be understood by one of skill in the art that the computer product integrates the hardware via generally understood devices in the art (i.e. attached to the analog device via an analog to digital converter).

The computer product is integrated into the water-based system on a device-by-device basis. As previously set forth, the acceptance criteria of all devices used in the drug product manufacture for the purposes of the water-based process are determined by the quality control unit. The analysis of the software and hardware occurs using any of the methods disclosed herein. (See for example FIG. 1 and FIG. 3). The program monitors and processes the data and stores the data using standard methods. The data is provided to an end user or a plurality of end users for assessing the quality of data generated by the device. Furthermore, the data is stored for comparative analysis to previous batches to provide a risk-based assessment in case of failure. Using the historical analysis will provide a more streamlined water-based process and will monitor to ensure that ingredients are mixed properly. In addition, the invention comprises monitoring the data from initial process, monitoring the data at the end process, and monitoring the data from a routine maintenance schedule to ensure the system maintain data integrity and validation standard predetermined by the quality control unit.
MES:

In one embodiment, the monitoring and analysis of the water-based systems achieves a step of integration into a manufacturing execution system whereby manufacturing productivity and product quality are increased. Costs are streamlined over time.

Example 15

Integration of Methods and Program into Finishing and Packaging System

Background:

Finishing and packaging of pharmaceuticals are important aspects of the pharmaceutical manufacturing process given that the finished product is ultimately distributed to the consumer. The need for safe uniform packaging is apparent to one of skill in the art.

Integration:

In one embodiment, the computer product is integrated into the finishing and packing system hardware. It will be understood by one of skill in the art that the computer product integrates the hardware via generally understood devices in the art (i.e. attached to the analog device via an analog to digital converter).

The computer product is integrated into the finishing and packing system on a device-by-device basis. As previously set forth, the acceptance criteria of all devices used in the drug product manufacture for the purposes of the finishing and packing process are determined by the quality control unit. The analysis of the software and hardware occurs using any of the methods disclosed herein. (See for example FIG. 1 and FIG. 3). The program monitors and processes the data and stores the data using standard methods. The data is provided to an end user or a plurality of end users for assessing the quality of data generated by the device. Furthermore, the data is stored for comparative analysis to previous batches to provide a risk-based assessment in case of failure. Using the historical analysis will provide a more streamlined finishing and packing process and will monitor to ensure that ingredients are mixed properly. In addition, the invention comprises monitoring the data from initial process, monitoring the data at the end process, and monitoring the data from a routine maintenance schedule to ensure the system maintain data integrity and validation standard predetermined by the quality control unit.

MES:

In one embodiment, the monitoring and analysis of the finishing and packing systems achieves a step of integration into a manufacturing execution system whereby manufacturing productivity and product quality are increased. Costs are streamlined over time.

Example 16

Integration of Methods and Program into Operational Units

Integration:

In one embodiment, the computer product is integrated into operational units. It will be understood by one of skill in the art that the computer product integrates said operational units via generally understood devices in the art (i.e. attached to the analog device via an analog to digital converter).

The computer product is integrated into the operational units on a device-by-device basis. As previously set forth, the acceptance criteria of all devices used in the drug product manufacture in an operational unit context are determined by the quality control unit. The analysis of the software and hardware occurs using any of the methods disclosed herein. (See for example FIG. 1 and FIG. 3). The program monitors and processes the data and stores the data using standard methods. The data is provided to an end user or a plurality of end users for assessing the quality of data generated by the device. Furthermore, the data is stored for comparative analysis to previous batches to provide a risk-based assessment in case of failure. Using the historical analysis will provide a more streamlined finishing and packing process and will monitor to ensure that the operational units are functioning properly for any given task. In addition, the invention comprises monitoring the data from initial process, monitoring the data at the end process, and monitoring the data from a routine maintenance schedule to ensure the system maintain data integrity and validation standard predetermined by the quality control unit.

MES:

In one embodiment, the monitoring and analysis of the operational units achieves a step of integration into a manufacturing execution system whereby manufacturing productivity and product quality are increased. Costs are streamlined over time.

Example 17

Integration of Methods and Program into Field Instrumentation Components

Integration:

In one embodiment, the computer product is integrated into field instrumentation components. It will be understood by one of skill in the art that the computer product integrates said field instrumentation components via generally understood devices in the art (i.e. attached to the analog device via an analog to digital converter).

The computer product is integrated into the field instrumentation components on a device-by-device basis. As previously set forth, the acceptance criteria of all devices used in the drug product manufacture in a field instrumentation components context are determined by the quality control unit. The analysis of the software and hardware occurs using any of the methods disclosed herein. (See for example FIG. 1 and FIG. 3). The program monitors and processes the data and stores the data using standard methods. The data is provided to an end user or a plurality of end users for assessing the quality of data generated by the device. Furthermore, the data is stored for comparative analysis to previous measurements to provide a risk-based assessment in case of failure. Using the historical analysis will provide a more streamlined and efficient field instrumentation components and will ensure that the field instrumentation components are functioning properly for any given task. In addition, the invention comprises monitoring the data from initial process, monitoring the data at the end process, and monitoring the data from a routine maintenance schedule to ensure the system maintain data integrity and validation standard predetermined by the quality control unit.

MES:

In one embodiment, the monitoring and analysis of the field instrumentation components achieves a step of integration into a manufacturing execution system whereby manufacturing productivity and product quality are increased. Costs are streamlined over time.

Example 18

Integration of Methods and Program into Cell Culture Systems

Background:

Understanding cell culture systems is vital for pharmaceutical manufacturing systems such as the production of monoclonal antibodies. Downstream integration of data including the monitoring of cell counts and culture progression. The ability for one of skill in the art to integrate this data into the downstream processes will inevitably create better yield and batch quality. It is an object of the invention to provide this advantage.

Integration:

In one embodiment, the computer product is integrated into the cell culture system hardware. It will be understood by one of skill in the art that the computer product integrates the hardware via generally understood devices in the art (i.e. attached to the analog device via an analog to digital converter).

The computer product is integrated into the cell culture system on a device-by-device basis. As previously set forth, the acceptance criteria of all devices used in the drug product manufacture for the purposes of the cell culture process are determined by the quality control unit. The analysis of the software and hardware occurs using any of the methods disclosed herein. (See for example FIG. 1 and FIG. 3). The program monitors and processes the data and stores the data using standard methods. The data is provided to an end user or a plurality of end users for assessing the quality of data generated by the device. Furthermore, the data is stored for comparative analysis to previous batches to provide a risk-based assessment in case of failure. Using the historical analysis will provide a more streamlined cell culture process and will monitor to ensure that the cell culture system data is integrated into downstream processes. In addition, the invention comprises monitoring the data from initial process, monitoring the data at the end process, and monitoring the data from a routine maintenance schedule to ensure the system maintain data integrity and validation standard predetermined by the quality control unit.

MES:

In one embodiment, the monitoring and analysis of the cell culture systems achieves a step of integration into a manufacturing execution system whereby manufacturing productivity and product quality are increased. Costs are streamlined over time.

Example 19

Integration of Methods and Program into a Manufacturing Execution System (MES)

Background:

A paradigm shift is needed in the way pharmaceuticals are manufactured. Current processes are not readily understood by the industry at-large and the processes are time consuming and produce lower quality products. One of ordinary skill will appreciate that a lower quality batch is essentially, a waste. Often the batch must be run again using different production and system parameters. Quality control units that can continuously monitor a specific manufacturing process and use that data, via data analysis methods disclosed herein, will allow pharmaceutical manufacturers to produce higher quality products in a faster timeframe. The fountainhead goal is to build quality into a pharmaceutical product, rather than test for quality after the product is made. One of ordinary skill on the art will understand that the former method is advantageous since it will be easier to locate a defect in manufacturing if monitoring is continuous rather that post-production or post-process. It is an object of the invention to provide this advantage.

Integration:

In one embodiment, the computer product is integrated into a manufacturing execution system that controls the pharmaceutical manufacturing process. It will be understood by one of skill in the art that the computer product integrates the hardware via generally understood devices in the art (i.e. attached to the analog device via an analog to digital converter).

The computer product is integrated into the manufacturing execution system on a device-by-device basis. As previously set forth, the acceptance criteria of all devices used in the drug product manufacture for the purposes of the manufacturing execution system are determined by the quality control unit. The analysis of the software and hardware occurs using any of the methods disclosed herein. (See for example FIG. 1 and FIG. 3). The program monitors and processes the data and stores the data using standard methods. The data is provided to an end user or a plurality of end users for assessing the quality of data generated by the device or devices. Furthermore, the data is stored for comparative analysis to previous batches to provide a risk-based assessment in case of failure. Using the historical analysis will provide a more streamlined pharmaceutical manufacturing process and will monitor to ensure that product quality is maximized. In addition, the invention comprises monitoring the data from initial process, monitoring the data at the end process, and monitoring the data from a routine maintenance schedule to ensure the system maintain data integrity and validation standards predetermined by the quality control unit.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

The invention claimed is:

1. A method of monitoring an acceptance criteria of a pharmaceutical manufacturing system said method comprising,
    a) monitoring data generated by a pharmaceutical manufacturing system during pharmaceutical manufacture, wherein said pharmaceutical manufacture produces an active ingredient;
    b) maintaining the data over time to provide a historical record;
    c) analyzing the historical record to provide a comparative analysis against an acceptance criteria;
    d) taking corrective action during pharmaceutical manufacture to obviate a rejection against the acceptance criteria whereby said corrective action comprises modifying said pharmaceutical manufacture.

2. The method of claim 1, wherein the monitoring is part of a quality assurance protocol.

3. The method of claim 1, wherein the historical record comprises a time stamped audit trail.

4. The method of claim 1, wherein the pharmaceutical manufacturing system uses at least a mixing tank and a time-stamped audit trail.

5. The method of claim 1, wherein said monitoring is at initial process.

6. The method of claim 1, wherein said monitoring is at end process.

7. A method comprising,
a) monitoring data generated by a pharmaceutical finishing and packaging system, wherein said finishing and packaging system produces a drug product;
b) maintaining the data over time to provide a historic record;
c) analyzing the historic record to provide a quality assurance determination for said drug product;
d) taking corrective action to obviate a failure against said quality assurance determination.

8. The method of claim 7, wherein said finishing and packaging system comprises a labeler.

9. The method of claim 7, wherein said finishing and packaging system comprises filling equipment.

10. The method of claim 7, wherein said finishing and packaging system comprises a vision inspection system.

11. The method of claim 7, wherein said finishing and packaging system comprises a capping machine.

12. The method of claim 7, wherein said historic record is maintained in a SQL database.

13. The method of claim 7, wherein said monitoring is continuous.

14. The method of claim 7, wherein said quality assurance determination is based on a quality assurance protocol.

* * * * *